(12) United States Patent
Krause

(10) Patent No.: US 9,482,260 B1
(45) Date of Patent: Nov. 1, 2016

(54) FLEXIBLE FASTENING DEVICE FOR INDUSTRIAL USE

(71) Applicant: William R Krause, Charlottesville, VA (US)

(72) Inventor: William R Krause, Charlottesville, VA (US)

( * ) Notice: Subject to any disclaimer, the term of this patent is extended or adjusted under 35 U.S.C. 154(b) by 169 days.

(21) Appl. No.: 14/073,797

(22) Filed: Nov. 6, 2013

Related U.S. Application Data

(63) Continuation-in-part of application No. 12/712,174, filed on Feb. 24, 2010, now abandoned.

(60) Provisional application No. 61/155,146, filed on Feb. 24, 2009.

(51) Int. Cl.
*F16B 35/04* (2006.01)
*A61B 17/72* (2006.01)
*A61B 17/86* (2006.01)

(52) U.S. Cl.
CPC ......... *F16B 35/041* (2013.01); *A61B 17/7225* (2013.01); *A61B 17/8625* (2013.01)

(58) Field of Classification Search
CPC .......... A61B 17/7225; A61B 17/8625; F16B 35/041
See application file for complete search history.

(56) References Cited

U.S. PATENT DOCUMENTS

| | | | |
|---|---|---|---|
| 4,175,555 A | 11/1979 | Herbert | |
| 4,328,839 A | 5/1982 | Lyons | |
| 4,959,064 A * | 9/1990 | Engelhardt | A61B 17/86 411/544 |
| 5,871,486 A | 2/1999 | Huebner | |
| 6,053,922 A * | 4/2000 | Krause | A61B 17/164 464/78 |
| 6,447,518 B1 | 9/2002 | Krause | |
| 8,382,742 B2 * | 2/2013 | Hermann | A61B 17/1631 606/1 |
| 8,551,142 B2 | 10/2013 | Altarac et al. | |
| 8,801,716 B2 * | 8/2014 | Meridew | A61B 17/1635 408/204 |
| 8,961,516 B2 * | 2/2015 | Nelson | A61B 17/7233 606/64 |
| 8,979,930 B2 * | 3/2015 | Glazer | A61F 2/442 623/17.11 |
| 9,078,740 B2 * | 7/2015 | Steiner | A61B 17/8875 |
| 2001/0018588 A1 | 8/2001 | Harder | |
| 2003/0187447 A1 | 10/2003 | Ferrante et al. | |
| 2005/0056979 A1 | 3/2005 | Frigg et al. | |
| 2005/0154390 A1 | 7/2005 | Biedermann | |
| 2005/0203517 A1 | 9/2005 | Jahng et al. | |
| 2006/0149265 A1 | 7/2006 | James et al. | |
| 2006/0293657 A1 | 12/2006 | Hartmann | |
| 2007/0016190 A1 | 1/2007 | Martinez et al. | |
| 2007/0016204 A1 | 1/2007 | Martinez et al. | |
| 2007/0083207 A1 | 4/2007 | Ziolo et al. | |
| 2008/0188895 A1 * | 8/2008 | Cragg | A61B 17/70 606/246 |
| 2008/0234752 A1 | 9/2008 | Dahners | |
| 2009/0118771 A1 | 5/2009 | Gonzalez-Hernandez | |
| 2009/0149890 A1 | 6/2009 | Martin | |
| 2010/0069970 A1 | 3/2010 | Lewis et al. | |
| 2011/0144703 A1 * | 6/2011 | Krause | A61B 17/8625 606/309 |
| 2011/0184472 A1 | 7/2011 | Niederberger et al. | |
| 2014/0114312 A1 * | 4/2014 | Krause | A61B 17/8625 606/62 |

* cited by examiner

*Primary Examiner* — Andrew Yang
(74) *Attorney, Agent, or Firm* — Sheldon H. Parker, Esq

(57) ABSTRACT

A flexible fastening device having multiple segments, one or more of which are flexible and one or more segments that also include threads. The flexibility is created through the use of at least one helical slot formed generally in the center segment of the element. Additional flexible segments also have at least one helical slot in either the same helical rotation and pattern or in an opposite rotation and/or different pattern. An elastomeric material can fill the hollow body, extend into the slots and/or encompass the exterior. The flexible fastening device can have a hollow body, including leading and trailing edge, or can have a partially hollow body.

12 Claims, 29 Drawing Sheets

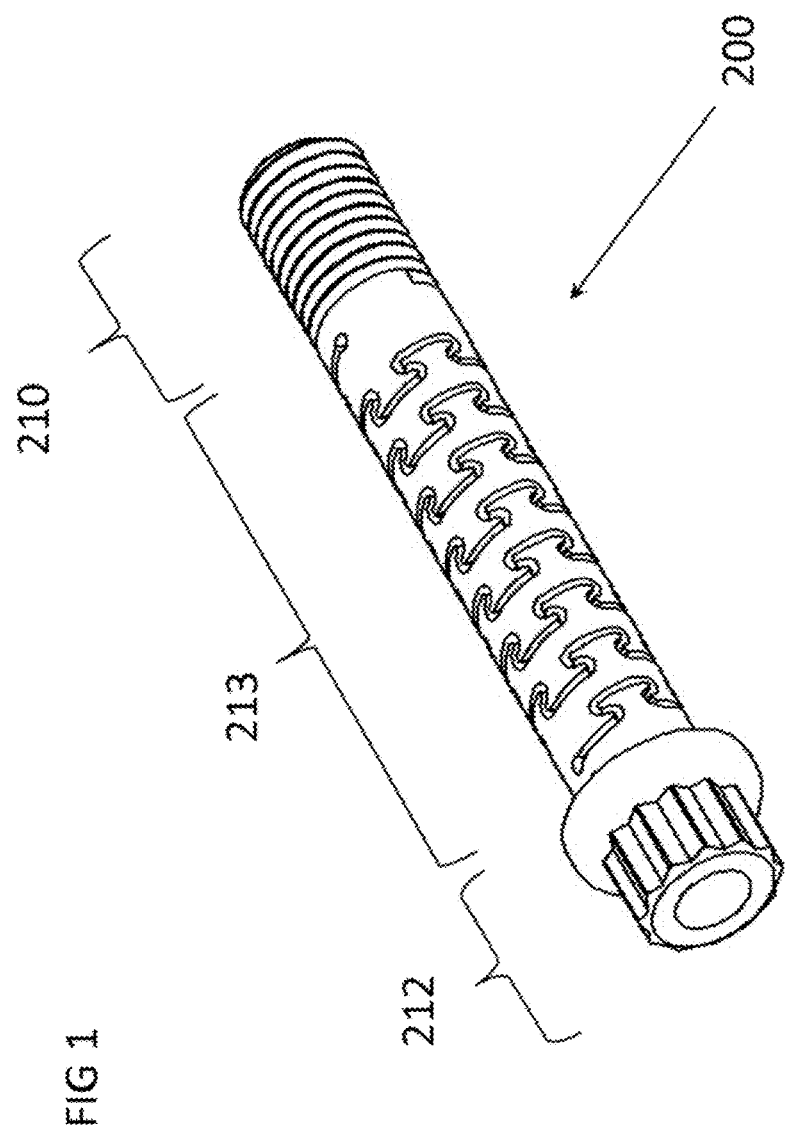

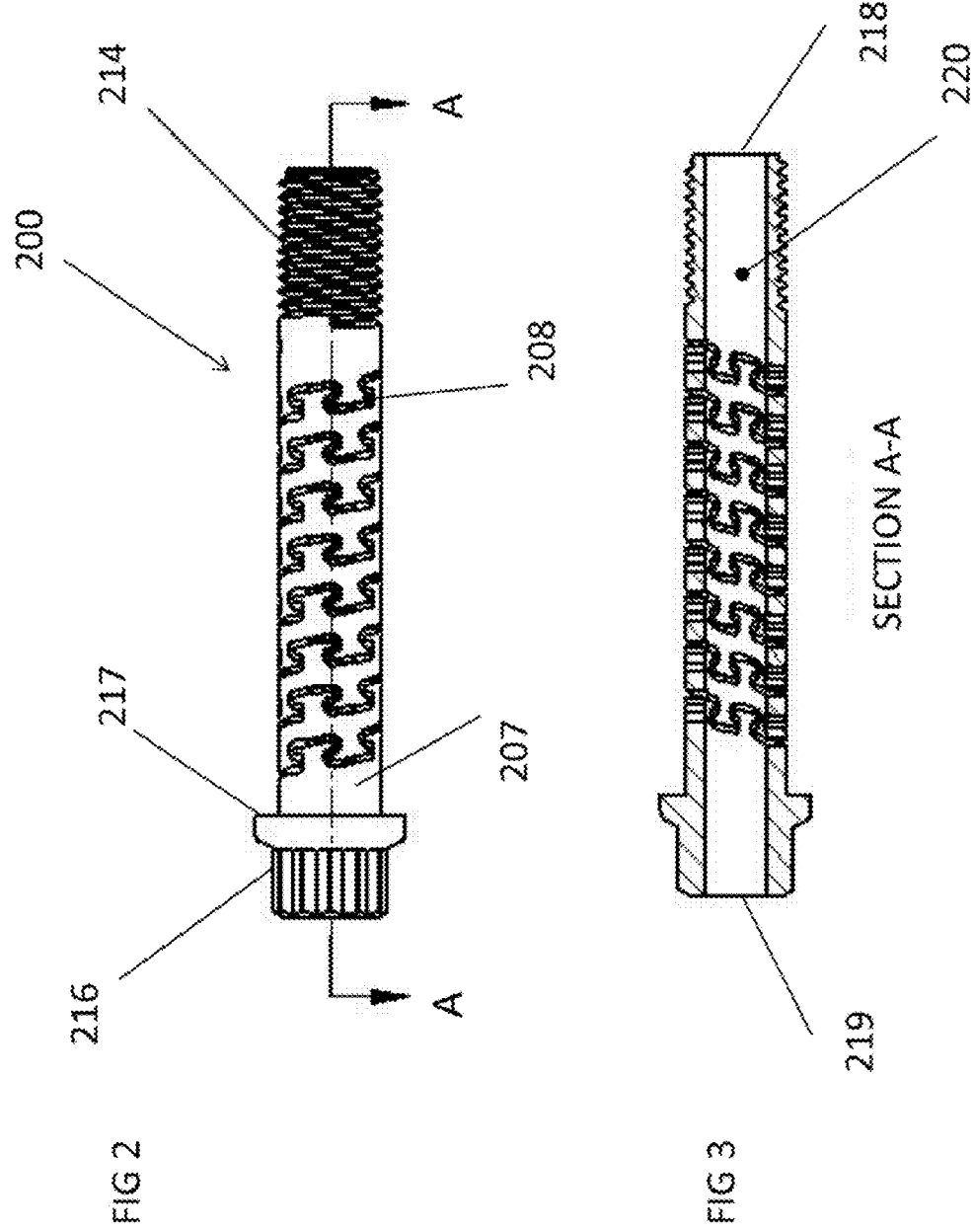

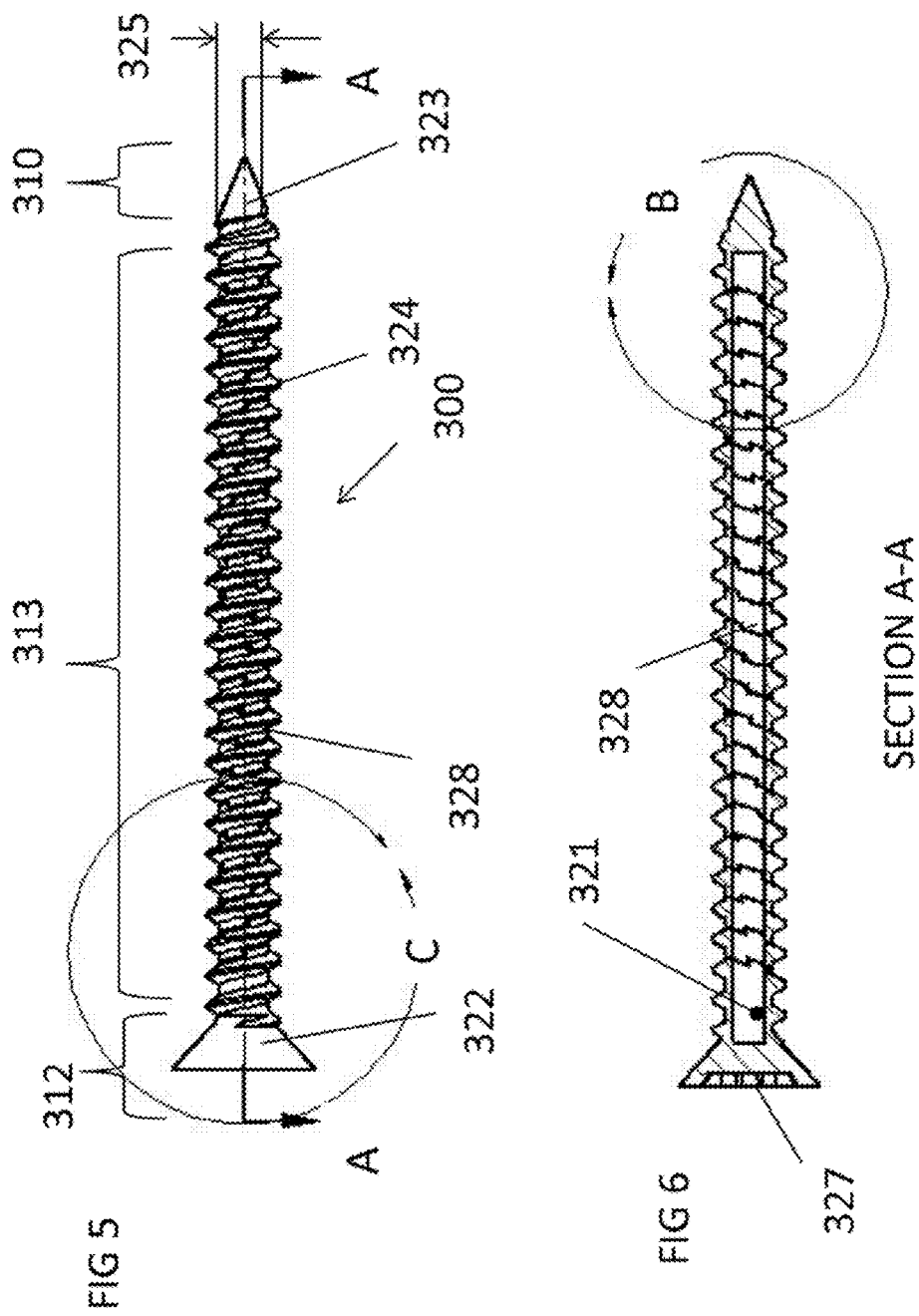

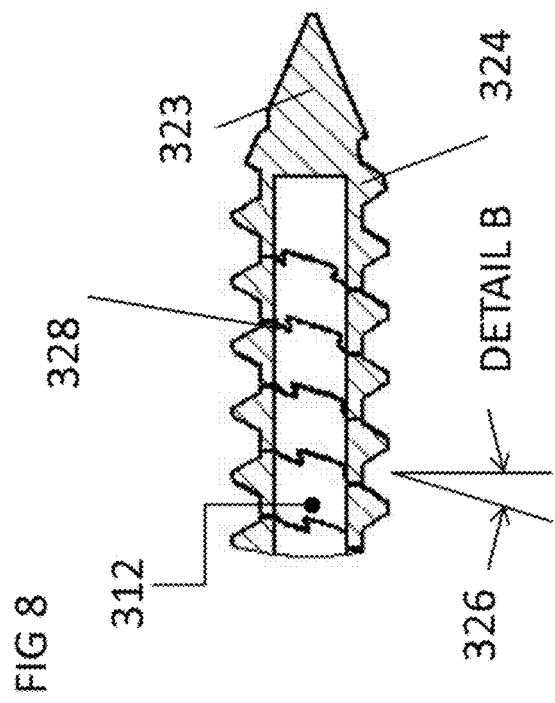
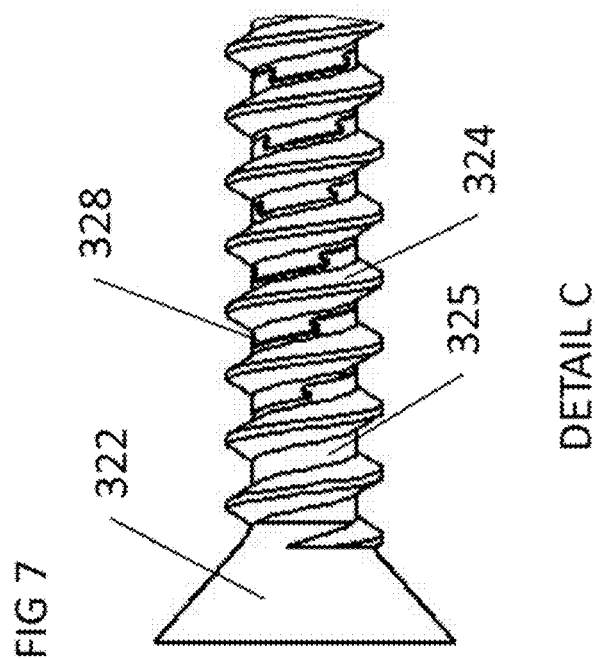

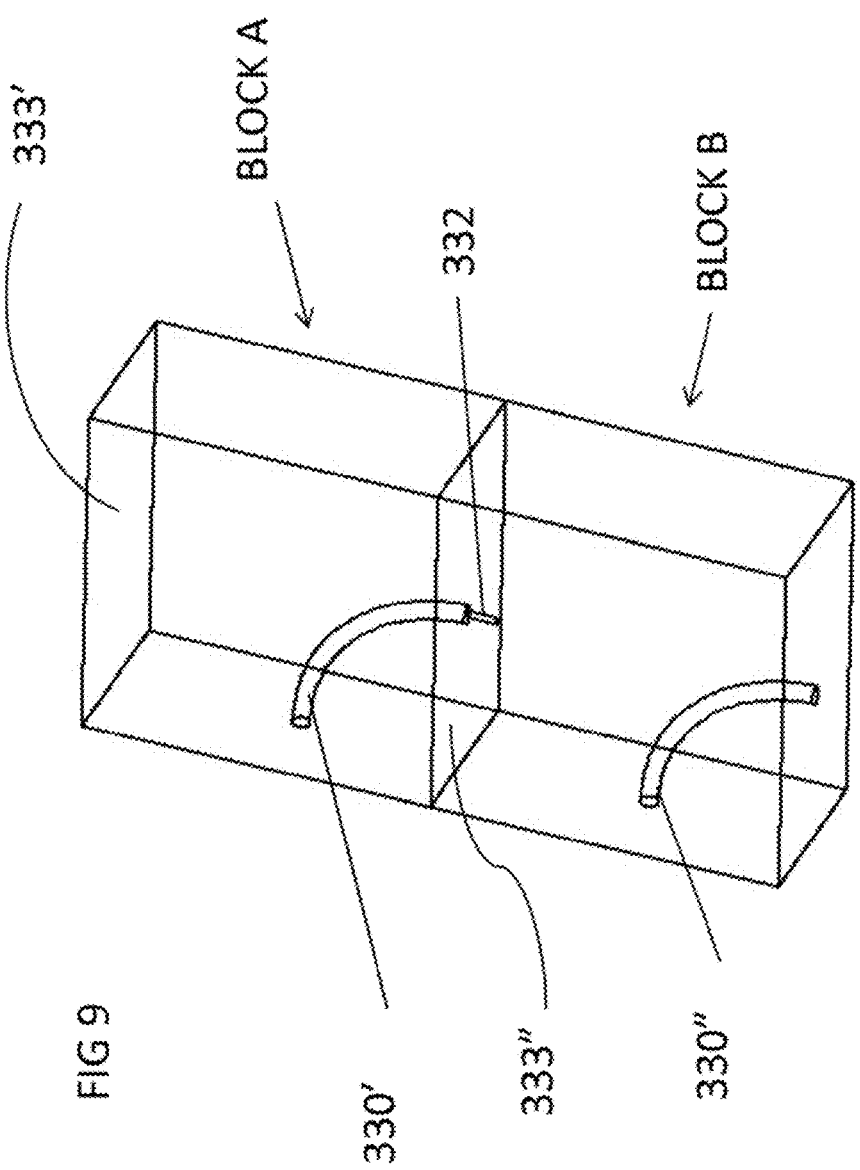

FIG 21
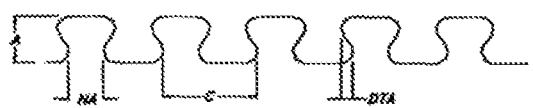
Figure 21A
Figure 21B
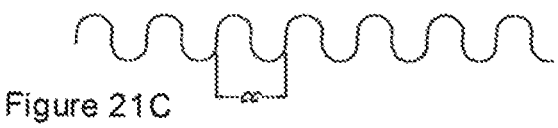
Figure 21C
Figure 21D
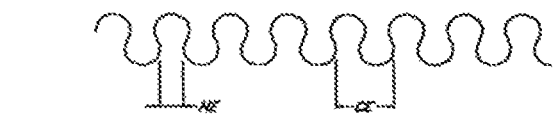
Figure 21E
Figure 21F

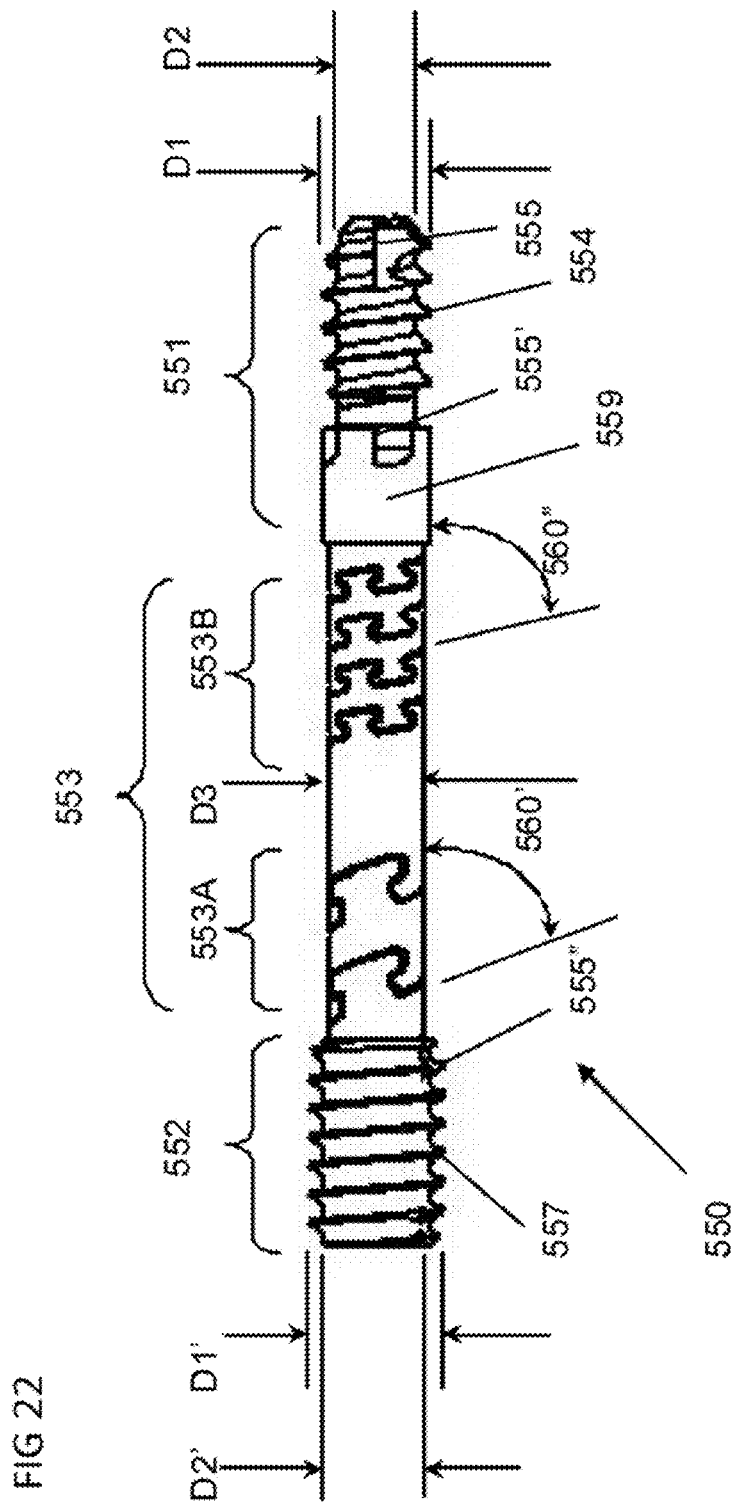

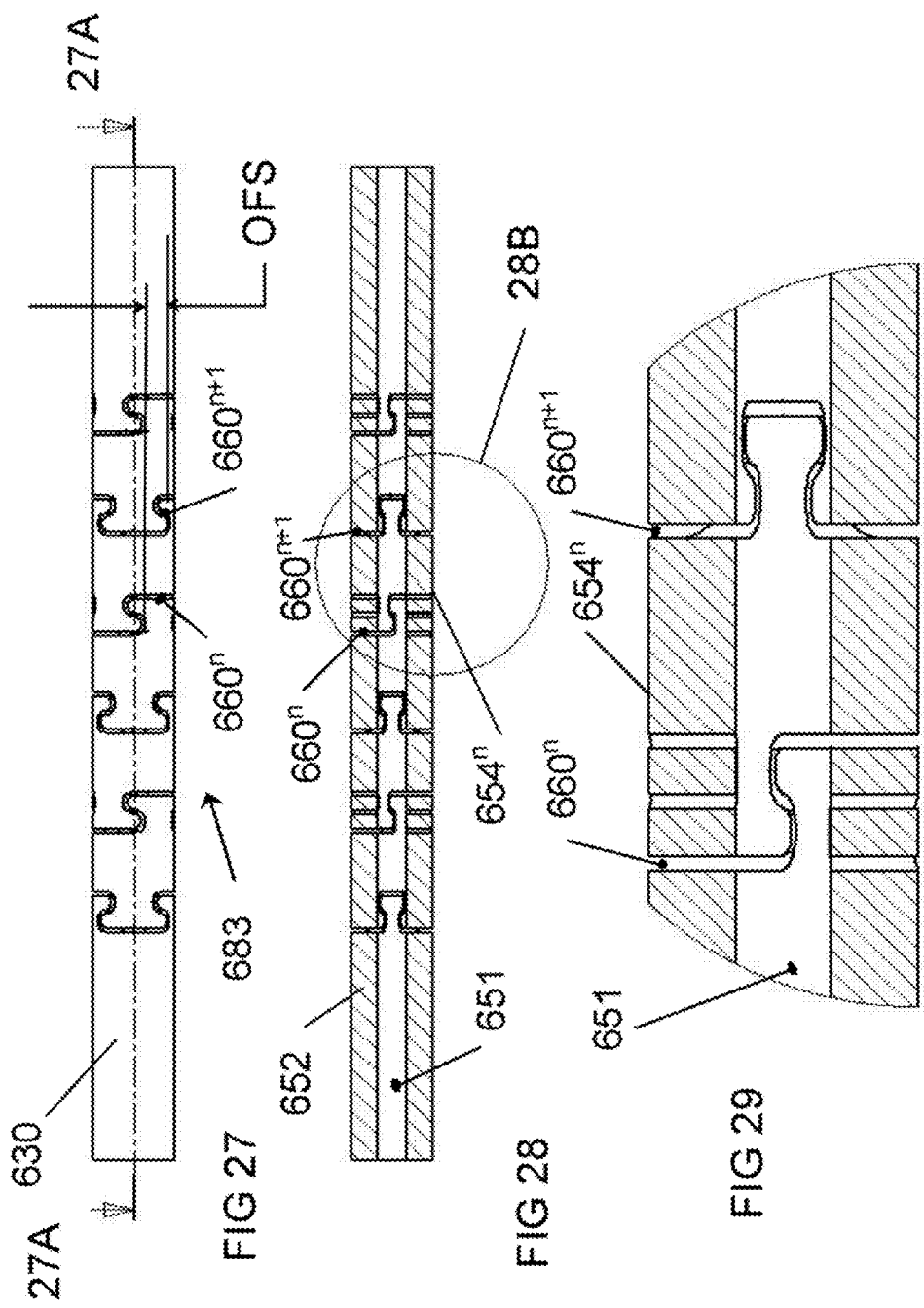

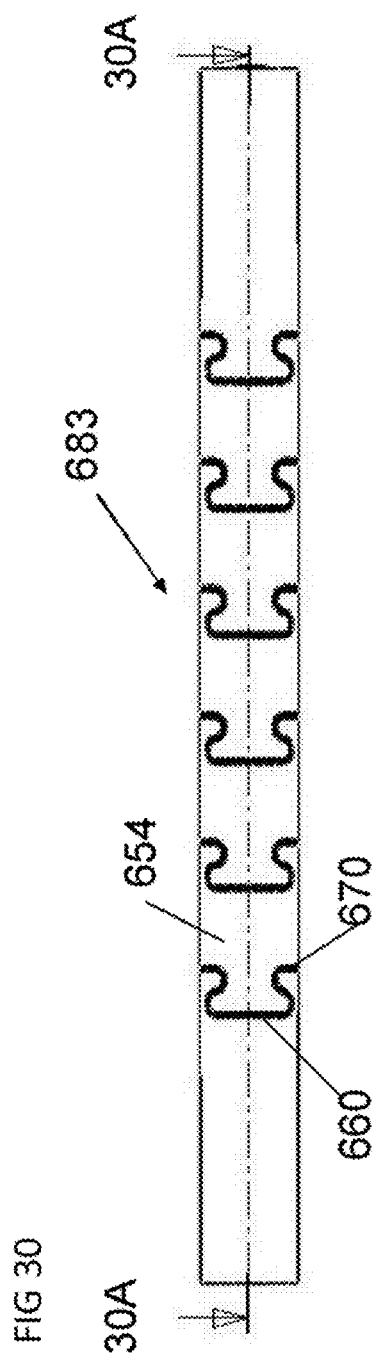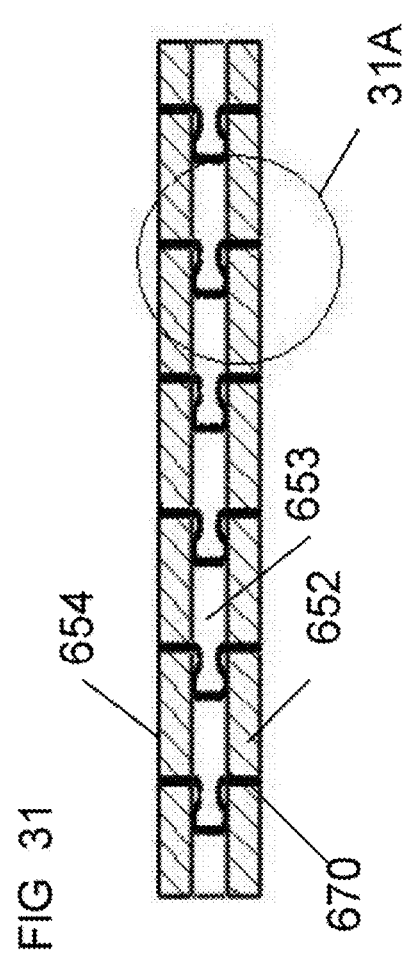

FLEXIBLE FASTENING DEVICE FOR INDUSTRIAL USE

CROSS REFERENCE

This application is continuation in part of U.S. Ser. No. 12/712,174 filed Feb. 24, 2010 which is a non-provisional of provisional application 61/155,146 filed on Feb. 24, 2009 both of which are incorporated herein as though recited in full.

FIELD OF INVENTION

This invention relates to a flexible fastening device which two components are held together.

DESCRIPTION OF THE RELATED ART

A screw, or bolt, is a type of fastener characterized by a helical ridge, known as an external thread or just thread, wrapped around a cylinder. Some threads are designed to mate with a complementary thread, known as an internal thread, often in the form of a nut or an object that has the internal thread formed into it. Other threads are designed to cut a helical groove in a softer material as the screw is inserted. The most common uses of bolts and screws are to hold objects together and to position objects. Threaded fasteners either have a tapered shank or a non-tapered shank. Fasteners with tapered shanks are designed to either be driven into a substrate directly or into a pilot hole in a substrate. Mating threads are formed in the substrate as these fasteners are driven in. Fasteners with a non-tapered shank are designed to mate with a nut or to be driven into a tapped, threaded hole.

The application of flexible fastening devices encompasses a broad spectrum of industries, included, but not limited to, manufacturing, construction, mining, transportation, agriculture, aviation, automotive, and medical. Flexible fastening devices, either tipped like screws and or flat end like bolts, have the characteristics in which the cylindrical portion of the device is bendable about the longitudinal length. Flexible fastening devices are useable in many applications, from manufacturing to medical, to secure to objects together.

In manufacturing and construction, fastening devices are used to join curved members together, to join misaligned holes, to absorb vibration between two components and numerous other applications. In addition, flexible devices are used to connect two or more members where by a straight passage of the bolt is impossible and a curved passage in one member allows the inserted flexible screw or bolt to follow the passage and be joined to another member.

In the medical industry, flexible screws are particularly useful in the intramedullary fixation of fractured or severed bone fragments. Bone screws are typically used in internal fixation to anchor the fixation system to the relevant bone portions or to join two or more fragments of a fractured bone into close proximity for bone union. For example, screws can be used in plate or rod systems to treat complex fractures of long bones or conditions such as vertebral instability. In small bone fractures, such as the bones of the hands, feet and wrist, the screw is placed across the fracture site to bring the fracture surfaces in close proximity. In medium (clavicle, rib and others) and long (lower and upper extremities) bone fractures, screws can be inserted into the intramedullary canal for minimally invasive fracture reduction.

In terms of design, the screw is broken up into two major segments, a head segment which links to the fixation element, and a stem segment (or shaft) which anchors into the bone. The design of the shaft is particularly important in terms of short term and long term viability, with the short term stability dictated solely by mechanical considerations and the long term stability determined by a combination of mechanical (e.g. fatigue strength of the screw) and biological (e.g. bone/screw interface) considerations.

As an example, hitherto, bone screws have been one of four typical forms. One of these has a thread only at its leading end, the head at the trailing end being separated from the thread by a smooth, cylindrical shank. It will be clear that such a bone screw, by threading wholly in the remote bone fragment and extending freely through the near fragment, can provide compressive action upon the fractured faces to be united.

The second type of bone screw has a cylindrical stem or shaft threaded over its full length. Such a screw can only be used to apply compression between two bone fragments if the near fragment is "over drilled" so that the thread engages solely in the remote fragment, the near fragment being free to move over the stem of the screw during insertion.

The third type of bone screw, commonly called a compression screw or Herbert screw (U.S. Pat. No. 4,175,555), has a region of large pitch and small diameter thread near the leading end and a region of smaller pitch and larger diameter thread near the trailing end, with the regions being separated by an unthreaded segment. The Herbert screw, however, suffers from a number of disadvantages. In the Herbert screw, the leading threads have a smaller diameter than the trailing threads. This is necessary to permit the leading threads to pass through the relatively large bore in the near bone fragment and engage the smaller bore in the remote bone fragment. The larger trailing threads then engage the larger bore in the near bone fragment As a result of this arrangement, any stripping of the threads cut into the bones during installation of the screw occurs in the remote bone, causing the necessity of drilling another bore. When stripping occurs in the bore in the near bone fragment, a screw having a head thereon could still be used to compress the fracture even though the near bore was stripped. However, when stripping occurs in the bore in the remote bone, the option of using a standard screw with the head thereon is eliminated.

The fourth type of bone screw has a cylindrical or tapered stem or shaft threaded with a variable pitch, course at the leading end and decreasing toward the trailing end, over its entire length. The Huebner screw (U.S. Pat. No. 5,871,486), sold under the trademark ACUTRAK, in most versions, is fully threaded and has a changing pitch over the entire length. The outside diameter of the thread tapers from front to rear so that as the trailing threads ream the tracks left by the leading threads due to the pitch change, the trailing threads are expanding outward into undisturbed material. The ACUTRAK screw can be driven in as far as desired without reduction in compression because of the expanding thread diameter along its length. In addition, the screw generates compression over the entire length, rather than only at the tip and tail as with Herbert.

A common characteristic of all the bolts and screws commercially available is that the shaft connecting the leading end to the trailing end is a straight, rigid structure. However in some applications it may be desirable that the screw is inserted into a curved structure. When the channel the device is to be inserted into is curved or misaligned, a straight, rigid device cannot be used. In the case of a bone screw, unless the screw is initially inserted precisely along the center axis of the curved bone after reducing the fracture, the screw will cause the bone to rotate to align itself with the screw thus causing the fracture to open. Another disadvantage of the prior art screws is that they generally follow the straight path and exit out of the side of the bone or enter the cortex of the bone, thus further weakening the bone.

The present invention overcomes the deficiencies and problems evident in the prior art as described herein above by combining the following features into an integral, longitudinally, laterally and torsionally flexible segment of the component.

SUMMARY OF THE INVENTION

The disclosed fastening device provides a screw or bolt that is flexible and will follow the curvature of a custom internal channel, the interior of a curved tubular structure or will allow some longitudinal flexibility between two mating components. The disclosed screw uses a modification of the flexible shaft technology as taught by Krause et al in U.S. Pat. Nos. 6,053,922 and 6,447,518 by imparting a serpentine, helical slot along a segment or segments of the component (screw) to form a flexible shaft. Preferably, the flexible shaft is formed by laser cutting an elongated tubular member of substantial wall thickness, to form the slot around and along the tubular member. A serpentine or sinuous path can also be superimposed on a circumferential slot about the circumference of the shaft in the form of a generally sinusoidal wave. Preferably, the sinusoidal wave forms dovetail-like teeth, which have a narrow base region and an anterior region that is wider than the base region. Thus, adjacent teeth interlock. The teeth can have a configuration as illustrated in U.S. Pat. No. 4,328,839, the disclosure of which is incorporated herein by reference, as though recited in detail.

The flexible fastening device, said flexible fastening device is manufactured from a rigid material and has a body with a length and a diameter, multiple segments and a length to diameter aspect of at least 2. One of the segments is a leading segment and another a trailing segment with a receiving area to receive a rotational force device. One or more segments can be between the leading and trailing segments, some of which are hollow. The segments can have the same or different diameters from adjoining segments and at least one of the multiple segments has exterior threads. The leading segment and/or the trailing segments can have cutting recesses. The body can also have a constant taper from the trailing edge to the leading edge.

At least one the hollow segments has at least one helical, sinuous slot to form a flexible segment. When multiple segments have helical slots, the slots can have a different pattern than, and spaced from, adjacent slots. The space between slots is inflexible. The helical angle of the slots range from about 5 degrees to about 20 degrees and the ratio of the amplitude of sinuous path to the pitch of the slot is in the range from greater than 0.1 to about 0.8.

In one embodiment the leading segment and the trailing segment have threads. In yet another, the threads of the leading segment can have a different pitch and amplitude than the threads of the trailing portion.

A slot of substantial length and width extends in a generally helical, sinuous, serpentine or other predetermined path, either continuously or intermittently, around and along the tubular member. The slot can follow the pitch of the adjacent threads or be of a different pitch such that the slot cuts through the thread. Alternatively, the slot or series of slots can extend in a circumferential manner around the tubular member. Advantageously, the slot is cut at an angle normal to the shaft using a computer controlled cutting technique such as laser cutting, water jet cutting, milling or other means. Additionally, this slot may be cut at an angle to the normal so as to provide an undercut slot; preferably the angle is in the range from about 5 to about 45 degrees from the normal. The sinuous pattern is about 1 to about 10 cycles per longitudinal revolution.

A plurality of slots can be employed thereby increasing the flexibility of the component, relative to a shaft having a single slot of identical pattern. The serpentine path forms a plurality of teeth and complimentary recesses on opposite sides of the slot. The slot has sufficient width to form an unbound joint permitting limited movement in any direction between the teeth and the recesses, thereby providing limited flexibility in all directions upon application of tensile, compressive, and/or torsion forces to said component. In a similar manner the slot can have increased width in one direction compared to another direction thus providing increased flexibility in one direction.

The flexible segment can have different degrees of flexibility along the length of said shaft. The varied flexibility can be achieved by having the pitch of the helical slot vary along the length of the shaft. The varied flexibility corresponds to the variation in the pitch of the helical slot. The helical path can have a helix angle in the range of about 10 degrees to about 45 degrees, and the helix angle can be varied along the length of the shaft to produce correspondingly varied flexibility. Alternatively, the width of the helical slot can vary along the length of the shaft to provide the varied flexibility. The rigidity of the flexible shaft can be achieved through the design of the slot pattern, thereby enabling the use of thinner walls than would otherwise be require to produce equivalent rigidity. In a preferred embodiment, the ratio of the amplitude of the serpentine path to the pitch of the slot is in the range from greater than 0.1 to about 0.8.

In one embodiment the slot can be filled with a resilient material, partially or entirely along the path of the slot. The resilient material can be an elastomer compound which can be of sufficient thickness to fill the slot and to encapsulate the entire shaft thus forming an elastomer enclosed member. The elastomer can be a resilient material such as a urethane or a silicone compound. The rigidity of the flexible shaft can be further achieved or varied through the use of filler material having different stiffness properties, thereby enabling the use of thinner walls than would otherwise be require to produce equivalent rigidity. The use of an elastomer is disclosed in co-pending application Ser. No. 12/069,934 and provisional 61/077,892, which are incorporated herein as though recited in full.

Preferably, the flexible segment is formed by laser cutting an elongated tubular member of substantial wall thickness, to form the slot around and along the tubular member in a helical manner. A serpentine path can be superimposed on a helical wave in the form of a generally sinusoidal wave. The slot may have the same pitch as the threads of the screw and be formed on the root diameter of the screw.

Preferably, the sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

The flexible device can be configured a number of ways, including but not limited to:

A first of the multiple segments being a leading segment having exterior threads; a second, or more, of the multiple segments be a center segment having the helical slot and exterior threads, and a third of the multiple segments being a trailing segment with exterior threads.

A first of the multiple segments is a leading segment having with exterior threads and a helical slot, the exterior threads having a first diameter; a second, or more, multiple segments being a center segment, having a helical slot and exterior threads having a second diameter; a third segment being a trailing segment with exterior threads having a third diameter.

A first segment being a leading segment with exterior threads and a helical slot; a second, or more, of the multiple segments is a center segment with a helical slot; and a third segment being a trailing segment.

A first has exterior threads and a helical slot; a second, or more, is a center segment; and a third is a trailing segment.

A leading segment has exterior threads, a second, or more, segment is a center segment, having said helical slot and a third trailing segments has is exterior threads.

A segment is a leading segment having with a helical slot and exterior threads, a second, or more, segment is a center segment having a helical slot and a third is a trailing segment having exterior threads.

To secure two bodies requiring a curved entry path, the desired entry path is created. A flexible fastening device is selected. The fastening devices has a body, with a length to diameter aspect of at least 2, and multiple segments. At least one of the multiple segments is hollow and has at least one helical, sinuous slot. At least one of the segments has exterior threads and the trailing segment has a rotational force receiving area. The fastening device is inserted into the entry path and rotated until the trailing end is adjacent to the start of the entry path.

An important aspect of this invention therefore lies in providing a screw for insertion in a curved channel that follows the curvature of the channel.

BRIEF DESCRIPTION OF THE DRAWINGS

Examples of the invention are illustrated in the drawings herewith. All of the figures are drawn on an oversized scale, and like structure in different figures bears like reference numerals.

FIG. 1 shows an isometric view of a bolt 200 having a driving head 212, an unthreaded, flexible shank 213, and a leading, threaded segment 210, in accordance with the invention.

FIG. 2 shows a side view of the flexible bolt 200. The flexible center segment 213 has a serpentine, spiral slot 208 though the shaft 207 of the center segment 213 generally from the proximal end of the leading end segment 211 to the distal end of the trailing segment 212. The leading end segment 210 has threads 214. In this illustration, the driving head 212 has an exterior spline 216 for mating with a driving device and a shoulder 217.

FIG. 3 is the segment view A-A of FIG. 2 showing a hollow cavity 220 extending through the screw 200 from the leading edge 218 to the trailing edge 219 in accordance with the invention.

FIG. 5 is a side view of screw 300 showing threads 324, slot 328, driving head 322, tapered end 323, sectional line A-A and detail area C in accordance with the invention.

FIG. 6 shows section A-A with internal cavity 321, slot 328 and detail area B in accordance with the invention.

FIG. 7 is the detail area C with driving head 322, slot 328, shank 325 and thread 324 in accordance with the invention.

FIG. 8 is the detail area B of FIG. 6 showing the internal cavity 312, tapered end 323, thread 324 and slot 328 in accordance with the invention.

FIG. 9 illustrates an application where by block A needs to be connected to block B (depicted as wire frame models to show the interior channel) for which using a straight bolt from the BLOCK A to BLOCK B would be impractical or impossible and a flexible bolt 340 could be passed through the curved channel 330' to connect the two blocks in accordance with the invention.

FIG. 22 is a side view of another embodiment of the flexible screw illustrating dual serpentine patterns having separated by a nonflexible segment in accordance with the invention in accordance with the invention.

FIG. 27 is an illustration of variation of the change in orientation of the circumferential serpentine slot relative to the adjacent slot whereby the teeth of each adjacent circumferential slot is staggered or offset a variable distance in accordance with the invention.

FIG. 28 is a cross sectional view of the central segment through the longitudinal axis of the device of FIG. 27

FIG. 29 is an exploded view of detail 28B showing the gap and interlocking of the serpentine slot of two slots that have been offset or staggered in accordance with the invention.

FIG. 30 is a schematic representation of the central segment of FIG. 25, showing general pattern of the circumferential serpentine slots with an elastomer filler material in the slot in accordance with the invention.

FIG. 31 is a sectional illustration though the longitudinal axis 30A-30A shown in FIG. 30 of the central segment showing the slot with a resilient filler in a portion of the slot in accordance with the invention in accordance with the invention.

DESCRIPTION OF THE PREFERRED EMBODIMENT

Figure 4:
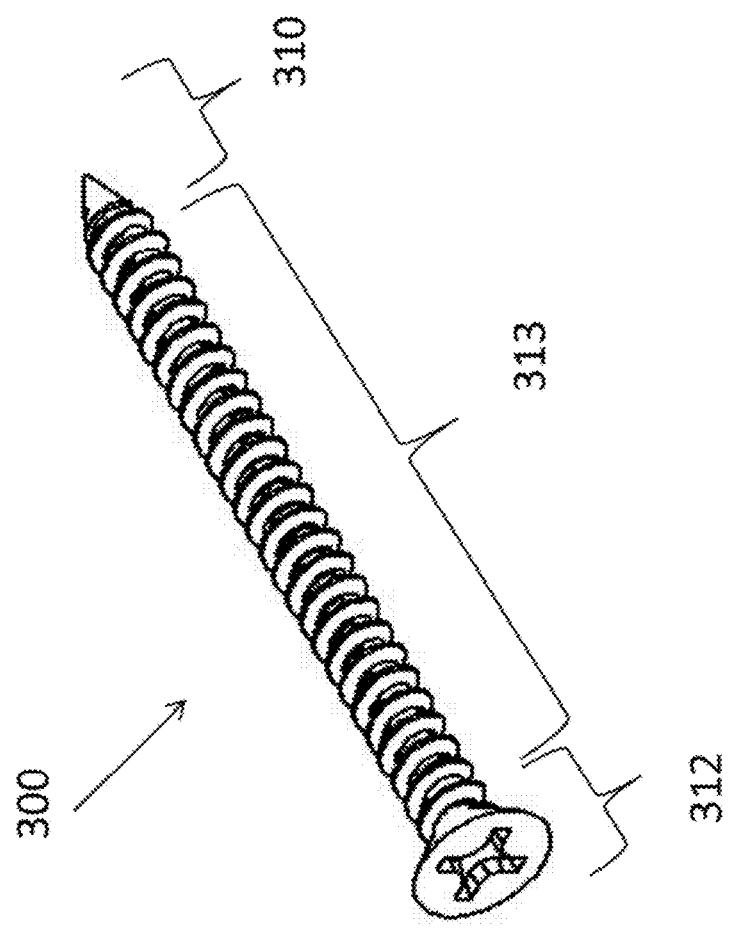
FIG. 4 is an isometric view of the screw 300 having a driving head 312, a threaded flexible shank 313, and a leading tapered segment 310 in accordance with the invention.

The flexible fastening device is composed of a rigid material with a body having a diameter, a length, and multiple defined segments, at least one of which has at least one helical slot to form a flexible segment with exterior threads on at least one of the segments. The leading segment is typically tapered in the case of a screw to provide for forward penetration into the material and is designed to cut a helical groove in a softer material as the screw is inserted. The leading segment may also have a blunt end, as in the case of a bolt, designed to mate with a complementary thread, known as an internal thread, often in the form of a nut or an object that has the internal thread formed into it. The trailing or driving segment is typically has a head shape, which may be pan, dome, round, truss (mushroom), flat (countersunk) or oval shaped, and has a receiving area to receive a rotational force device. The receiving area can employ a wide variety of drive designs, each requiring a different kind of tool to drive in or extract them. The most common screw drives are the slotted and Phillips in the US; hex, Robertson, and Torx are also common in some applications, and Pozidriv has almost completely replaced Phillips in Europe. The mid segment of the fastening device is the body or shank which connects the leading segment with the driving segment. The segment, or segments, of the flexible device having the one helical slot, or slots, are hollow to enable flexibility. The helical slot can have a sinuous configuration with about 1 to about 10 cycles per longitudinal revolution. The hollow body, in some embodiments hollow from the distal to proximal ends and in others hollow only at the flexible segments, can receive elastomeric material that can fill at least a portion of the hollow body, fill at least a portion of the at least one slot, and/or encompass at least a portion of the body. The length of the body can vary considerably in length from millimeters to meters and in diameter from millimeters to meters.

In some embodiments the segments that are the leading segment and trailing segment can each or both have at least one cutting recess. The leading segment and trailing segment can both have threads having the same or different pitch and amplitude than the threads of the other segment. Additionally, the second of at least one helical slot can a different pattern than, and be spaced from, the first of one helical slot in both the helical and serpentine patterns.

In some embodiments, the body can be tapered or each segment can be of a different diameter than the other segments. Example combinations of flexible and nonflexible include: 1) a first, leading, segment having exterior threads, a second segments having a helical slot, a third trailing segment having exterior threads; 2) a first, leading, segment having a helical slot and exterior threads, a second segments having a helical slot, a third trailing segment having exterior threads; 3) a first, leading, segment having exterior threads, a second segments having a helical slot and exterior threads, a third trailing segment having exterior threads; 4) a first, leading, segment having exterior threads with a first diameter and a helical slot, a second segments having a helical slot and exterior threads having a second diameter, a third trailing segment having exterior threads and a third diameter; 5) a first, leading, segment having exterior threads and a helical slot, a second segments having a helical slot, a third trailing segment; 6) a first, leading, segment having exterior threads and a helical slot, a second segment and a third trailing segment.

DEFINITIONS

For the purposes herein the term "flexible fastening device" or "device" can be used interchangeably and shall refer to an externally threaded fastener having at least one threaded segment and at least one slotted, flexible segment that may be threaded or unthreaded.

For the purposes herein the terms "slit" and "slot" are used interchangeably, consistent with their definitions, as follows: slot n. 1. A narrow opening; a groove or slit: a slot for coins in a vending machine; a mail slot. A gap between a main and an auxiliary airfoil to provide space for airflow and facilitate the smooth passage of air over the wing. The slot as disclosed must typically complete two rotations around the body, or shaft.

For the purposes herein the term pitch as used herein is defined as: pitch—n.1. The distance traveled by a machine screw in one revolution. 2. The distance between two corresponding points on adjacent screw threads or gear teeth. (American Heritage Dictionary, 3rd Edition, Copyright 1994) The pitch is generally relative to the diameter and range from 20% to 200% of the diameter.

For the purposes herein the term "cycle" shall refer to: Cycle—1. An interval of time during which a characteristic, often regularly repeated event or sequence of events occurs: Sunspots increase and decrease in intensity in an 11-year cycle. 2.a. A single complete execution of a periodically repeated phenomenon: A year constitutes a cycle of the seasons. 2b. A periodically repeated sequence of events: cycle includes two halves of the sine-wave like undulation of the slot path. (American Heritage Dictionary, 3rd Edition, Copyright 1994)

For the purposes herein the term "amplitude" shall refer to the maximum absolute value of the periodically varying quantity of the slot, and can be expressed as from 10% to 90% of pitch.

For the purposes herein the term "serpentine" shall refer to: 3 a: winding or turning one way and another <a serpentine road>b: having a compound curve whose central curve is convex. (Merriam-Webster online dictionary)

For the purposes herein the term "helical", "helix" and "spiral" and interchangeable and shall refer to: 1 a: winding around a center or pole and gradually receding from or approaching it <the spiral curve of a watch spring>b: helical c: spiral-bound <a spiral notebook>2: of or relating to the advancement to higher levels through a series of cyclical movements. (Merriam-Webster online dictionary)

For the purposes herein the term "compression device" refers to a threaded device the pulls and maintains two bodies together. A compression screw can be used in medical applications as well as non-medical applications, i.e. woodworking for use as a recessed screw head. A threads on the leading and trailing segments of a compression device will typically have with different pitches.

compression (lag) bone screw: used as a compressing unit between two fragments with the first half of the screw near the point threaded, with the diameter of the ridges greater than that of the unthreaded half near the head. As the ridged part of the screw bites in the walls of the drill hole in the distal fragment, the unthreaded part is free to move within the drill hole in the proximal fragment, thus compressing the two pieces of bone together. http://medical-dictionary.thefreedictionary.com/Howmett+compression+bone+screw For the purposes herein the term "segment" refers to a clearly differentiated subdivision of a part, one of several parts or sections into which the feature of an object is changed to another feature. For example changes in slot pattern and/or width, slot to non-slotted, hollow to solid, flexibility, diameter, incorporation of threads, thread dimensions, as well as other changes disclosed herein.

For the purposes herein the term "frequency" shall refer to the number of times a specified phenomenon occurs within a specified interval: Frequency. 1a Number of repetitions of a complete sequence of values of a periodic function per unit variation of an independent variable. 1b. Number of complete cycles of a periodic process occurring per unit time. 1c. Number of repetitions per unit time of a complete waveform, as of an electric current. The number of times the cycles form a repetitive pattern in one unit of length is the frequency of the slot pattern. The number of cycles "C" of the slot undulations superimposed upon the circumferential path which are present in one revolution around the shaft, is referred to as the cycles per revolution. (American Heritage Dictionary, 3rd Edition, Copyright 1994)

For the purposes herein the term "bolt" shall refer to an externally threaded fastener designed for insertion through the holes in assembled parts, and is normally intended to be tightened or released by torquing a nut.

A bolt is designed for assembly with a nut. A screw has features in its design which makes it capable of being used in a tapped or other preformed hole in the work. Because of basic design, it is possible to use certain types of screws in combination with a nut. Any externally threaded fastener which has a majority of the design characteristics which assist its proper use in a tapped or other preformed hole is a screw, regardless of how it is used in its service application.

Bolts have been defined as headed fasteners having external threads that meet an exacting, uniform bolt thread specification (such as ISO metric screw thread M, MJ, Unified Thread Standard UN, UNR, and UNJ) such that they can accept a non-tapered nut. Screws are then defined as headed, externally threaded fasteners that do not meet the above definition of bolts. In common usage, the distinction (not rigorous) is often that screws are smaller than bolts, and that screws are generally tapered while bolts are not.

The primary characteristics of a bolt are:

An externally threaded fastener, which because of head design or other feature, is prevented from being turned during assembly, and which can be tightened or released only by torquing a nut, is a bolt. (Example: round head bolts, track bolts, plow bolts).

An externally threaded fastener, which must be assembled with a nut to perform its intended service, is a bolt. (Example: heavy hex structural bolt).

For the purposes herein the term "screw" shall refer to an externally threaded fastener capable of being inserted into holes in assembled parts, of mating with a preformed internal thread or forming its own thread, and of being tightened or released by torquing the head.

The Primary characteristics of a screw are:

An externally threaded fastener, which has a thread form which prohibits assembly with a nut having a straight thread of multiple pitch length, is a screw. (Example: wood screws, tapping screws).

An externally threaded fastener, which must be torqued by its head into a tapped or other preformed hole to perform its intended service is a screw. (Example square head set screw).

[U.S. Customs and Border Protection Agency (CBP) (2011-02), *What Every Member of the Trade Community Should Know About: Distinguishing Bolts from Screws*, An Informed Compliance Publication (2011-02 ed.), Washington, DC, USA: CBP.gov.]

While the present invention will be described more fully hereinafter with reference to the accompanying drawings, in which particular embodiments and methods of implantation are shown, it is to be understood at the outset that persons skilled in the art can modify the invention herein described while achieving the functions and results of this invention.

Flexible fastening devices can be used in many applications to join curved members together, to join misaligned holes, to absorb vibration between two components, to join components that don't allow straight connection and numerous other applications.

Accordingly, the descriptions that follow are to be understood as illustrative and exemplary of specific structures, aspects and features within the broad scope of the present invention and not as limiting of such broad scope.

The invention in one embodiment relates to a flexible fastening device having a predominately blunt end, such as a bolt shape or a predominately pointed or sharply beveled end such as screw configuration having one or more flexible segments within the device. The flexible device has threaded as well as unthreaded segments that can be placed as needed, depending on end use.

The flexibility is created through the use of at least one helical slot formed in the hollow segment, or segments, of the body or shaft of the device. In other embodiments, additional flexible segments also have at least one helical slot in either the same helical rotation and pattern or in an opposite rotation and/or different pattern. In another embodiment the flexible segment has a flexible segment that has at least one helical, serpentine slot within a segment of the screw element that is embedded within a polymer or other flexible material so as to fill the slot with the flexible material as disclosed in U.S. Pat. Nos. 6,053,922 and 6,447,518 which are incorporated herein as though recited in full. In an additional embodiment the flexible fastening device uses a hollow flexible element that encompasses a polymer or other flexible material within its central core without extending into the helical slot(s). A further embodiment uses a flexible slotted segment within the element that contains a polymer or other flexible material within the central core with the flexible material extending radially outward through the helical, serpentine slot(s). The flexible fastening device can further incorporate a flexible slotted segment that contains a polymer or other flexible material within the central core of the flexible segment that extends radially outward through the slot and encompasses the outer surface of the element and/or the flexible segment.

The flexible fastening device can have a hollow body, including leading and trailing edge, or can have a partially hollow body. The fastening devices manufactured with a partially hollow body would have solid leading and trailing segments that are welded onto the hollow flexible segment. Although the hollow segments of the body do not need to contain the helical slot, all segments of the body that have the helical slot must be hollow.

Numerous industrial applications are applicable for use with the disclosed flexible devices, including but not limited to any application where two pre-drilled members that require fixation are slightly out of align. The ability to construct the device with a small diameter in the order of one to two millimeters enables it to be used for fine, detailed work, such as guns clocks and other intricate machines, while the ability to enlarge the device enables it to be used for larger applications, such engines, furniture, automobiles, aircraft and such.

In FIG. 1, the described flexible fastening device 200 comprises leading end segment 210 and a trailing end segment 212 axially spaced apart by a substantially cylindrical body having a flexible center segment 213. The fastening device has a length and a diameter with a length to diameter aspect ratio of at least 2.

FIG. 2 shows a side view of the flexible fastening device 200 of FIG. 1. The flexible center segment has a serpentine, or sinuous, spiral slot 208 though the shaft 207 of the center segment 213 generally from the proximal end of the leading end segment 210 to the distal end of the trailing end segment 212. The leading end segment 210 has threads 214. In this illustration, the trailing end segment 212 has an exterior spline 216 for mating with a driving device and a shoulder 217. The spiral slot 208 though the shaft 207 extends generally from the proximal end of the leading end segment 210 to the shoulder 217 at the trailing end segment 212.

As seen in the sectional view A-A of FIG. 3, through the flexible device 200 is a hollow cavity 220 extending from the leading edge 218 of the leading end segment 210 to the trailing edge 219 of the trailing end segment 212. In this embodiment, the leading edge 218 is slightly beveled, however whether there is a bevel and the degree to which there is a bevel, will vary depending upon end use.

In the embodiment illustrated in FIGS. 4 5, and 6 the device 300 has a more conventional screw configuration with the leading end 310 having a tapered edge 323. The threads 324 run the length of the center segment 313 from the leading end 310 to the driving head 322. A serpentine slot 328 runs in a helical fashion within the root diameter 325 of the threads 324 to provide flexibility. Segments A-A and C are described in more detail in FIGS. 6 and 7, respectively.

FIG. 6 is a sectional view of axis A-A seen in FIG. 5 to illustrate the passage of the central cavity 321 from the leading tapered edge 323 extending though the hollow center segment 313 to the driving head 322. The driving end 322 of the device 300 is furnished with a hexagonal or similar receiving recess 327 to receive a screwdriver, or other rotational force device. To incorporate the hollow segment 321 into the device 300, the flexible segment 321, the leading tapered end 323 and driving head 322 all may be made separately in parts and joined together using traditional joining techniques such as precision welding.

FIG. 7 is a detailed view of detail C in FIG. 5 showing the serpentine, helical slot 328 within the root diameter 325 of the center segment 313 to provide the flexibility to the device 300.

FIG. 8 is a detailed drawing of the leading end of the device 300 in FIG. 6. The slot 328, having a predetermined width, is cut with a general helix angle 326 that corresponds to the pitch of the threads 324. The angle 326 may vary from 10 to 80 degrees with respect to the axis perpendicular to the longitudinal axis of the central segment 313. When the slot 328 is cut between the threads 324, the pitch of the slot 328 will generally be the pitch of the corresponding threads.

FIGS. 9 through 12 are an example of the application of the flexible device 400 joining two components together. FIG. 9 shows two components, BLOCK A and BLOCK B that need to be joined together but because of location or other reason, a straight bolt could not be inserted from the superior face 333' of BLOCK A into the superior surface 333" of BLOCK B. However, a curved channel 330' is incorporated in BLOCK A for the passage of a flexible bolt 340 into a pre-threaded hole 332 on the superior surface 333" on BLOCK B. In this illustration, BLOCK B has also been provided with a channel 330" that would be used to connect a third block.

Figure 10:
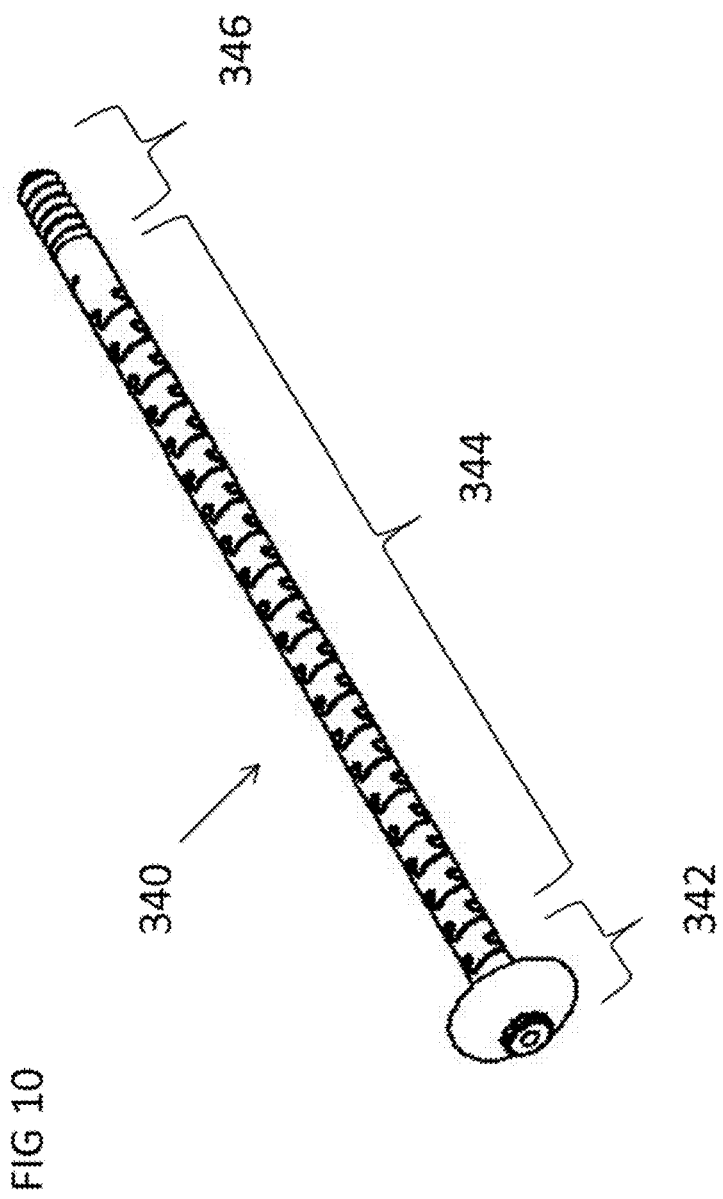
FIG. 10 shows flexible shaft 340 with driving head 342, flexible segment 344 and threaded end 346 in accordance with the invention.
Figure 11:
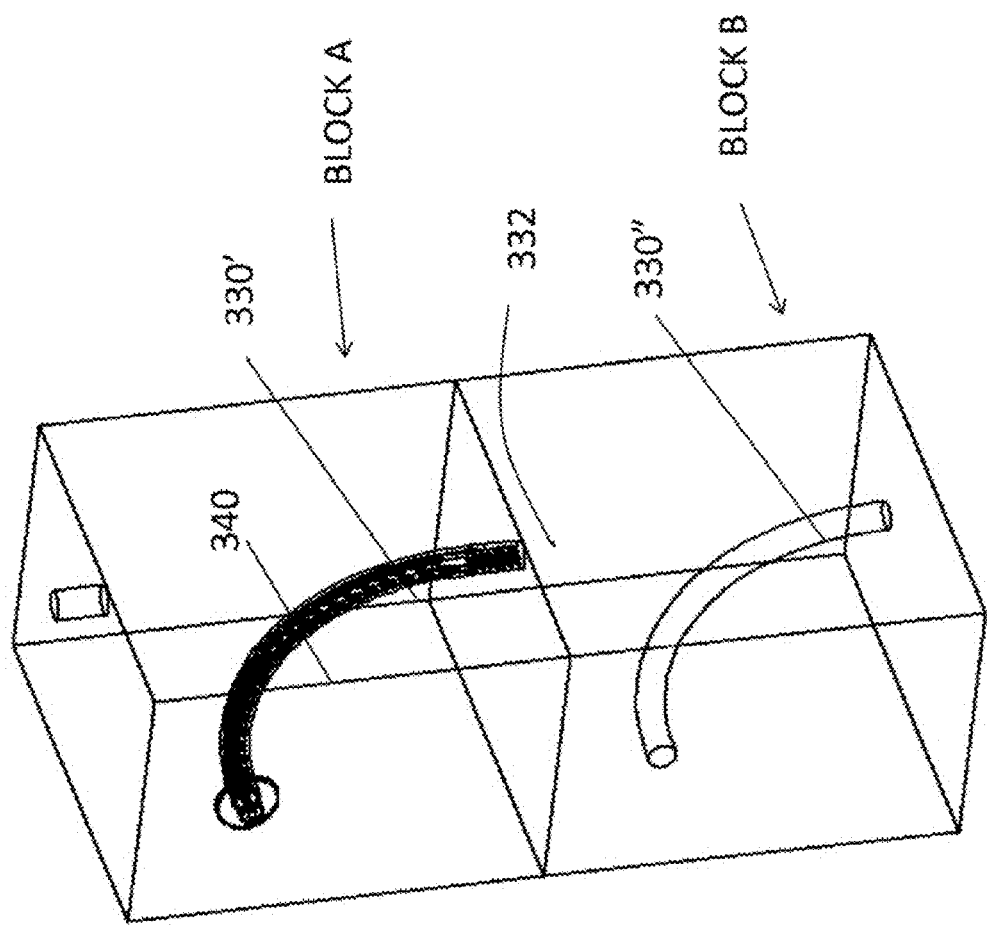
FIG. 11 illustrates how curved bolt 340 can be inserted through channel 330' of BLOCK A and fastened into hole 332 of BLOCK B to fasten the two components in accordance with the invention.
Figure 12:
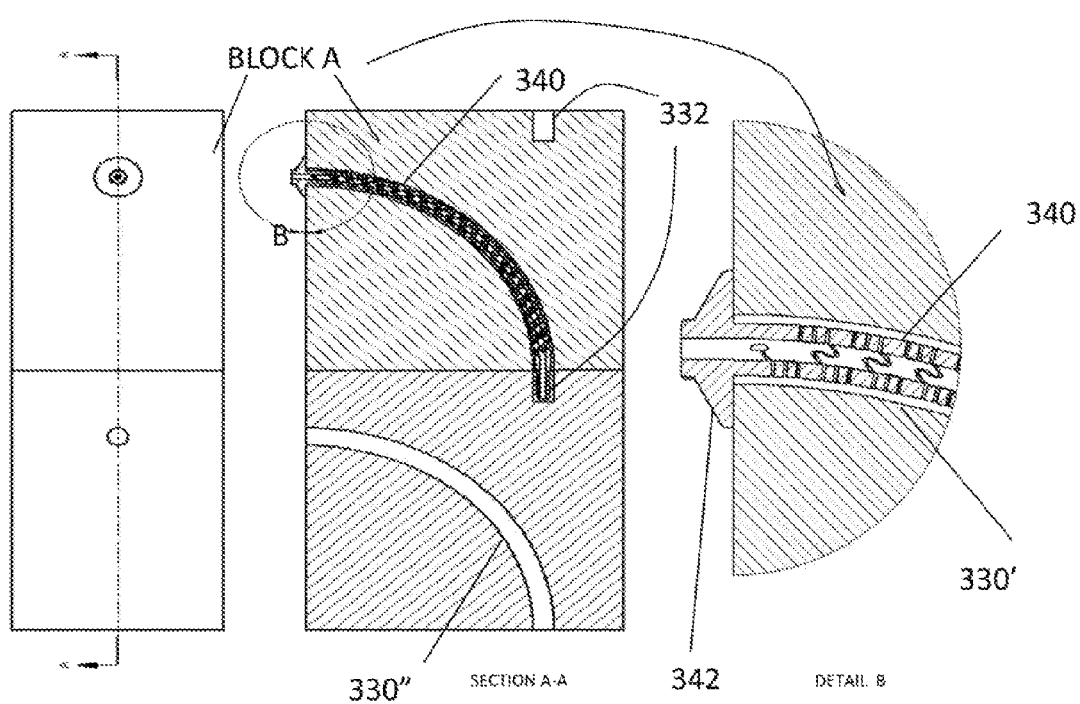
FIG. 12A shows a cutaway side view of section A-A of blocks A and B to show how a flexible bolt 340 can be used to hold two components together in accordance with the invention.
FIG. 12B shows a cutaway front view of section A-A of blocks A and B to show how a flexible bolt 340 can be used to hold two components together in accordance with the invention.
FIG. 12C shows a cutaway view of a flexible bolt 340 within a channel to hold two components together in accordance with the invention.

In an alternate device for securing the above blocks, FIG. 10 shows the flexible fastening device 340 with a non threaded, flexible segment 344, a driving head 342 and a distal non-flexible threaded end 346. Such a device 340 would be dimensioned to extend through channel 330' of BLOCK A for attachment to BLOCK B as shown in FIG. 11 and sectional view A-A in FIGS. 12A and 12B. FIG. 12 C shows DETAIL B in FIG. 12B with the device 340 in the channel 330' and the driving head 342 seated on BLOCK A. If required, the BLOCK B could be attached to an additional block or base to extend the components the drilled hole 330"

Figure 13:
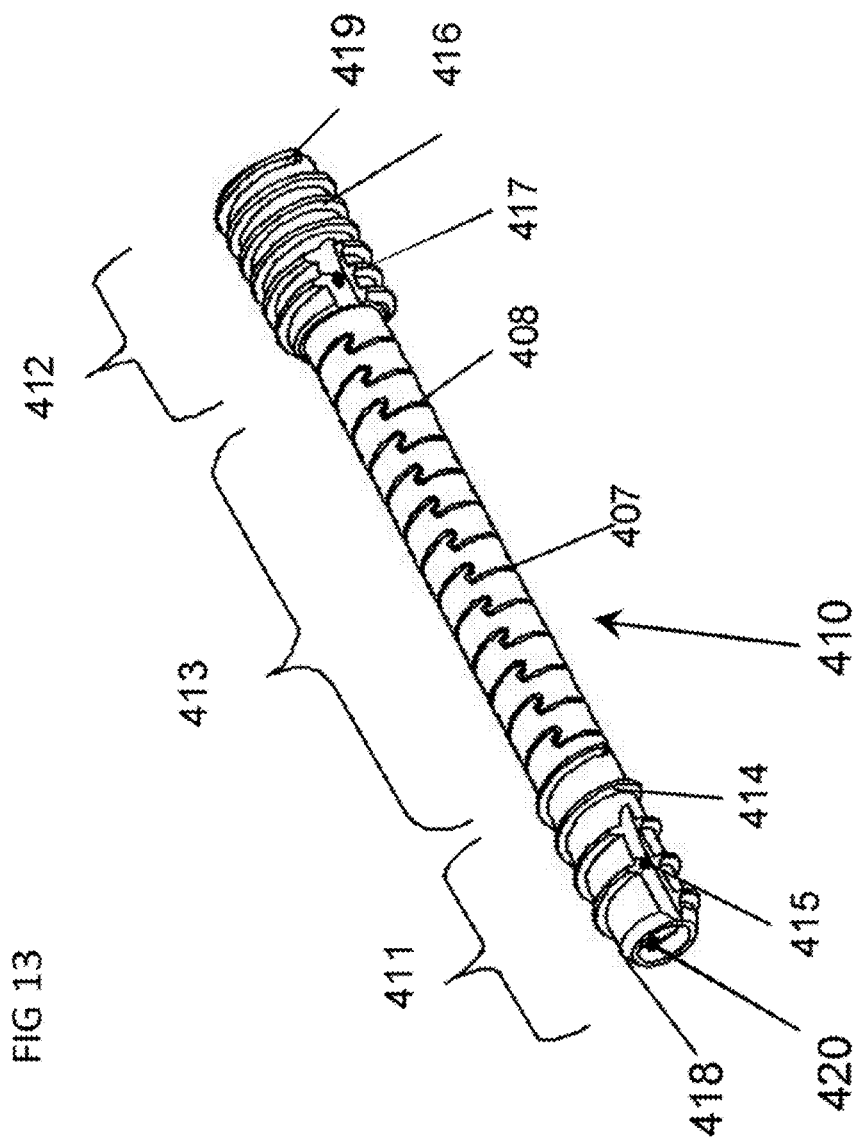
FIG. 13 is an isometric view of the flexible bone screw as describe in the present application in accordance with the invention.

In FIG. 13, the flexible device as described in this figure is directed to use as a flexible compression device 410 as can be used for compression of bone or tissue fragments. The device 410 comprises leading end segment 411 and a trailing end segment 412 axially spaced apart by a substantially cylindrical, flexible center segment 413. The leading end segment 411 is furnished with first screw thread 414 and a thread cutting recess 415 and the trailing end segment 412 has a second screw thread 416 and a thread cutting recess 417. The flexible center segment 413 has a serpentine, spiral slot 408 though the shaft 407 of the center segment 413 generally from the proximal end of the leading end segment 411 to the distal end of the trailing segment 412. Through the screw 410 is a hollow cavity 420 extending from the leading edge 418 to the trailing edge 419. In this, and other illustrated embodiments, the leading edge 418 is slightly beveled, however whether there is a bevel and the degree to which there is a bevel, will vary depending upon end use.

Figure 14:
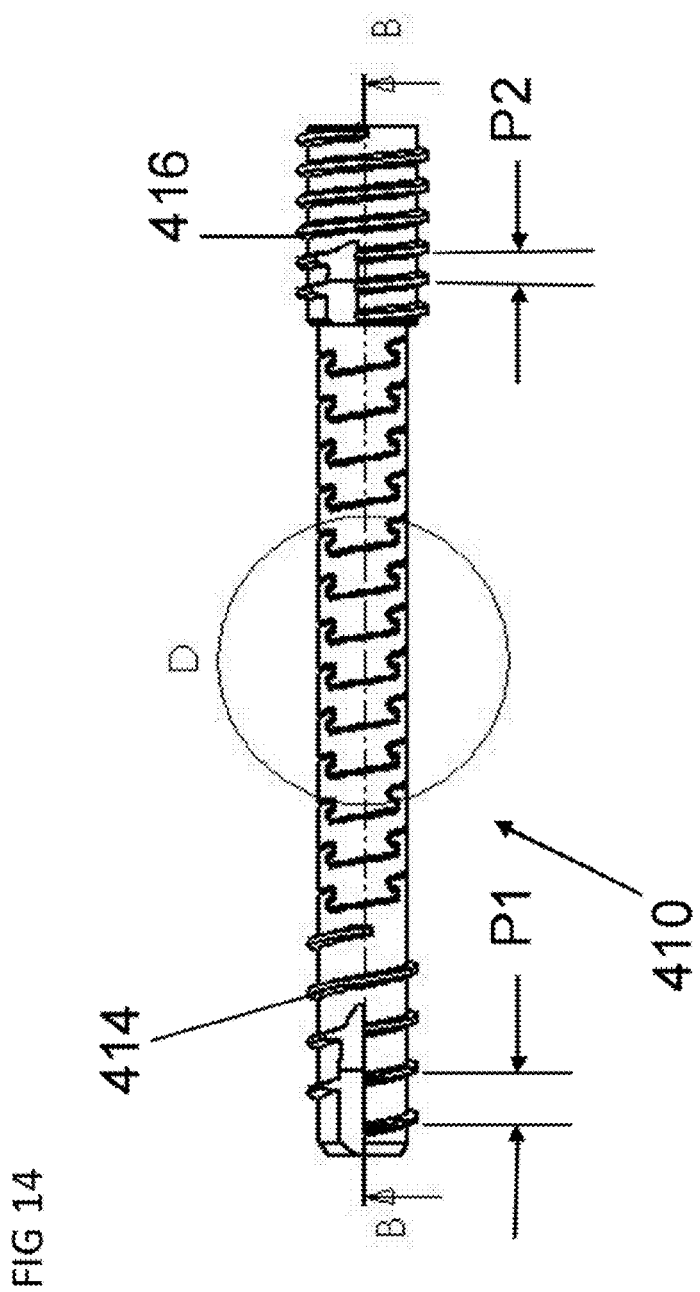
FIG. 14 is a side elevation view of a flexible compression bone screw shown in FIG. 13 in accordance with the invention.

As seen in FIG. 14, the threads 414 and 416, as are all threads disclosed herein, are like-handed. The device 410 is an embodiment intended to apply compressive action; and therefore the pitch P1 of thread 414 is typically slightly greater than the pitch P2 of thread 416. The proportions between the threads would typically be P1>P2 or P1<P2, although in some applications it can be beneficial for both P1 and P2 to be equal. Segments D and B-B are described in more detail in FIGS. 16 and 20, respectively.

Figure 15:
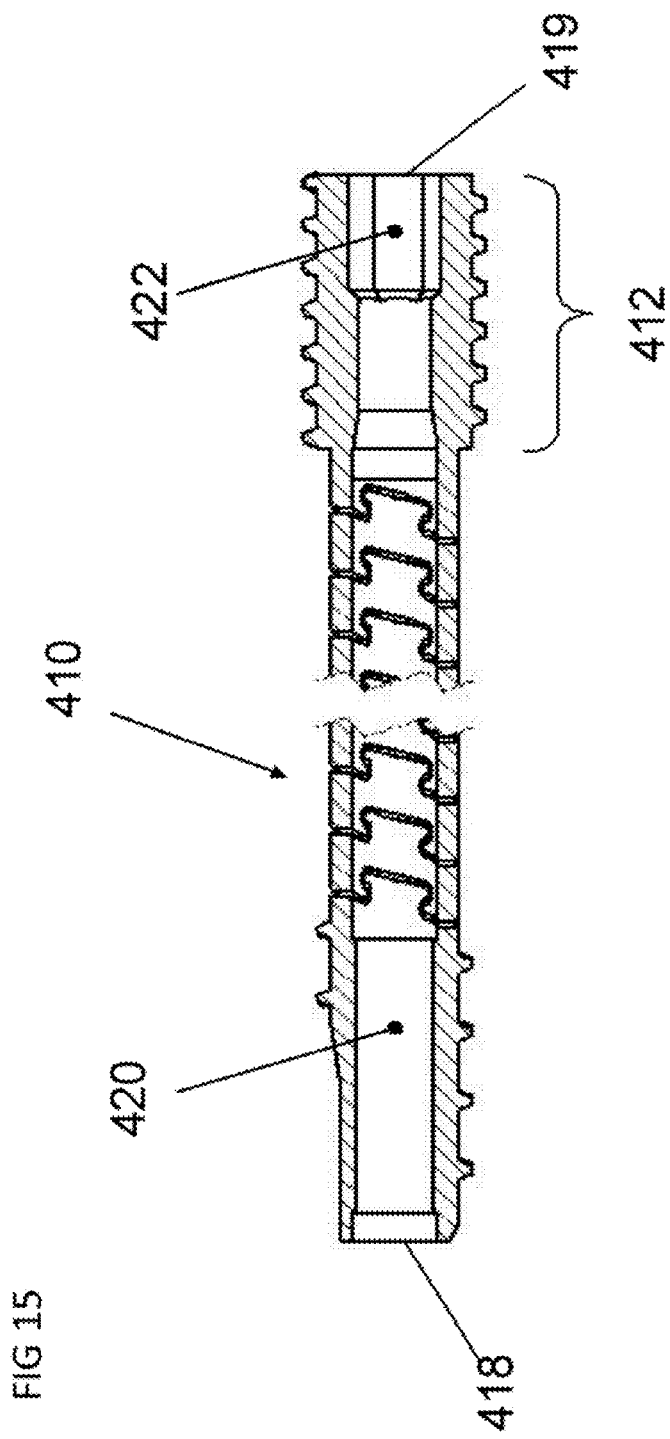
FIG. 15 is a sectional view of the flexible compression bone screw through the longitudinal plane B-B from FIG. 14 in accordance with the invention.

FIG. 15 is a sectional view of axis B-B as seen in FIG. 14 to illustrate the passage of the central opening 420 from the leading edge 418 extending though the device 410 to the trailing edge 419. The trailing end segment 412 of the bone device 410 is furnished with a hexagonal or similar receiving recess 422 to receive a screwdriver, or other rotational force device.

Figure 16:
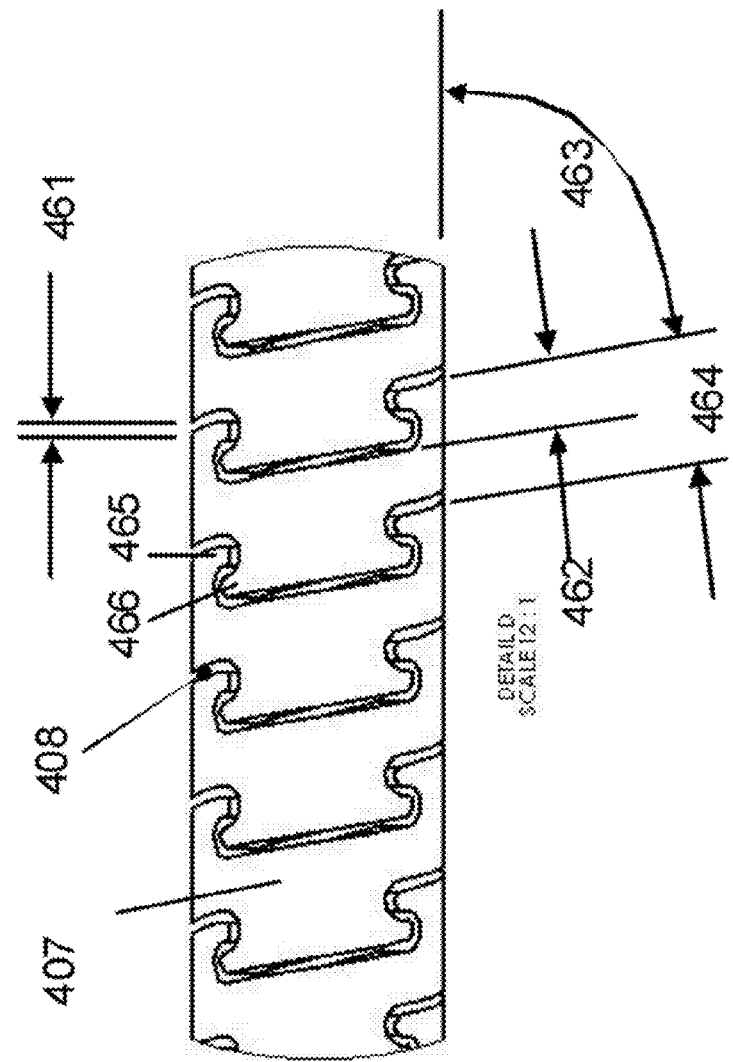
FIG. 16 is an exploded view of the section D shown in FIG. 14 in accordance with the invention.

FIG. 16 is an exploded view of section D of FIG. 14 showing the serpentine, helical slot 408 within the shaft 407 of the central flexible segment 413 of screw 410. The slot 408, having a width 461, is cut with a general helix angle 463 of about 10 to 80 degrees with respect to the longitudinal axis of the central segment 413. In this embodiment the slot 408 is cut in a serpentine pattern having an amplitude 462 and interlocking teeth 465, 466 with a pitch 464.

The slot 408 is representative of all the slots disclosed herein in that it is cut through the shaft 407 into the core 420. Although the slots disclosed herein are of different patterns, this is purely a function of flexibility and all have the same basic construction. In addition, the slot 408 can have a generally helical revolution in the clockwise rotation or in a generally counter clockwise orientation. In the following description of the criteria of the slots, no reference numbers specific to other figures are used, as the criteria are applicable to all slot configurations.

The helical path of the slot 408 is about 0.25 to about 5 cycles per diameter length. In order to provide the desired flexibility, while maintaining support, the width of the slot 408 should not exceed about 0.075 of an inch in a device having a diameter in the range from about 0.10 to about 0.50 inches, with a general width of about 0.005 to about 0.025 inches. Or alternatively stated, the slot 408 width is between about 0.5% and about 5.0% of the diameter of the element. The helical angle ranges from about 5 degrees to about 20 degrees.

Figure 17:
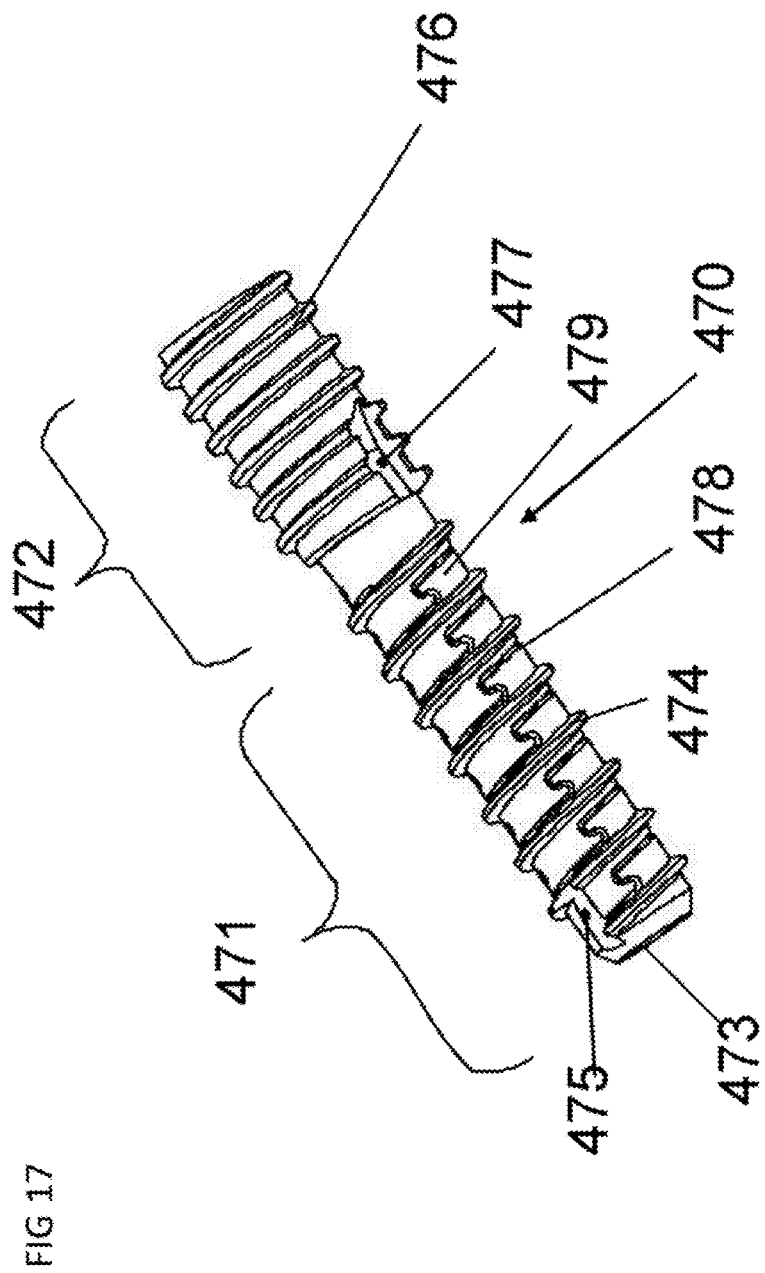
FIG. 17 is an isometric view the second embodiment of the flexible bone screw 470 as describe in the present application in accordance with the invention

FIG. 17 is an illustration of another embodiment of a flexible compression device 470 for use in pulling together and compressing two bodies. The device 470 has a leading flexible segment 471 and a trailing end segment 472. The leading flexible segment 471 is furnished with first screw thread 474 and a thread cutting recess 475. The trailing end segment 472 has a second, larger diameter screw thread 476 and a thread cutting recess 477 at the distal end of the segment 472. The leading segment 471 has a serpentine, spiral slot 478 though the shaft 479 from the leading edge 473 to the trailing end segment 472. Generally the pitch of the serpentine helical slot 478 will follow pitch of the helical thread 474. Alternatively, the pitch of the helical slot may be different from the pitch of the threads such that the slot cuts through the threads. Although the shaft 479 diameter can be increased, as in other embodiments, in this illustration only the minor diameter of the threads 476 is increased. In this, and subsequent embodiments, the thread 474 and slot 478 run along the flexible segment 471. This design provides stiffer flexing than in embodiments where only the slot runs in the flexing segment.

Figure 18:
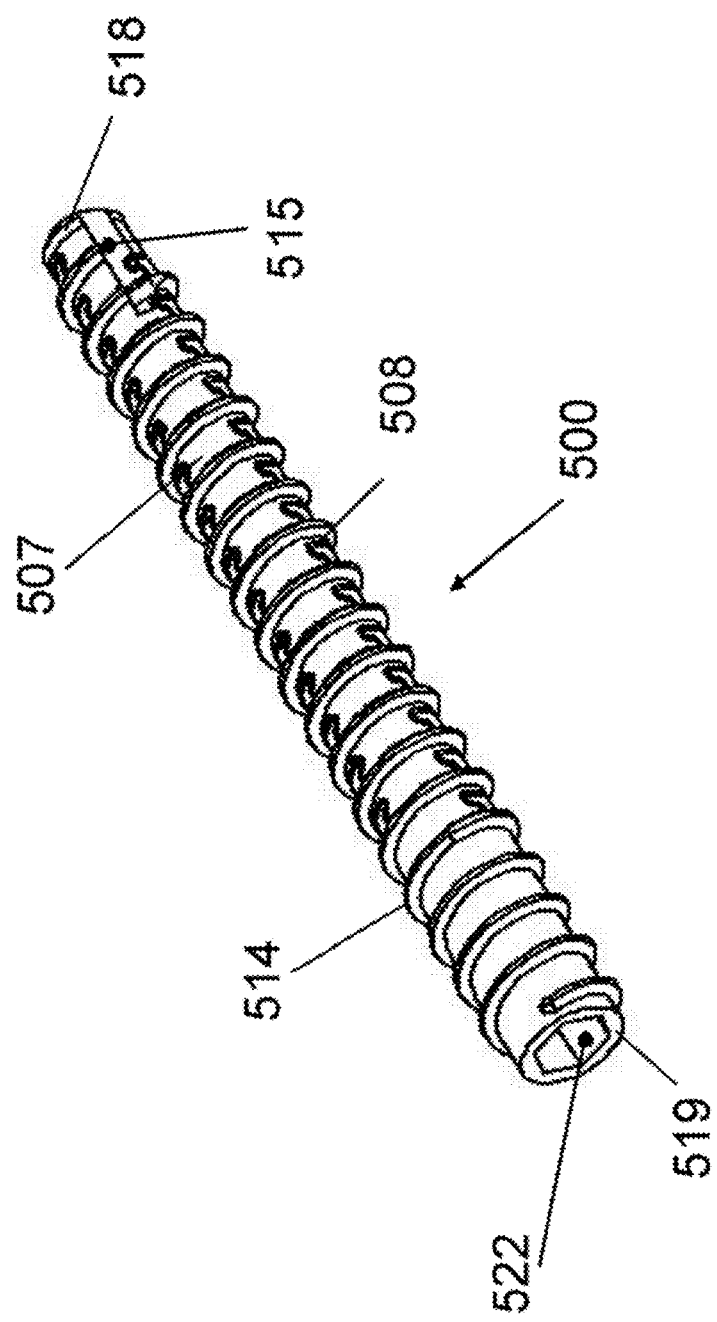
FIG. 18 is the isometric view of another embodiment of the flexible compression device having a tapered profile in accordance with the invention.

FIG. 18 is an illustration of an additional embodiment of the flexible compression device 500 having a tapered shaft 507 with the serpentine helical slot 508 extending along the shaft 507. The thread 514 is continuous from the smaller diameter leading edge 518 to the larger diameter trailing edge 519. The device 500 has a single thread cutting recess 515. Also shown is the hexagonal or similar recess 522 to receive a screwdriver or other rotational device used in the insertion or removal of the device 500.

Figure 19:
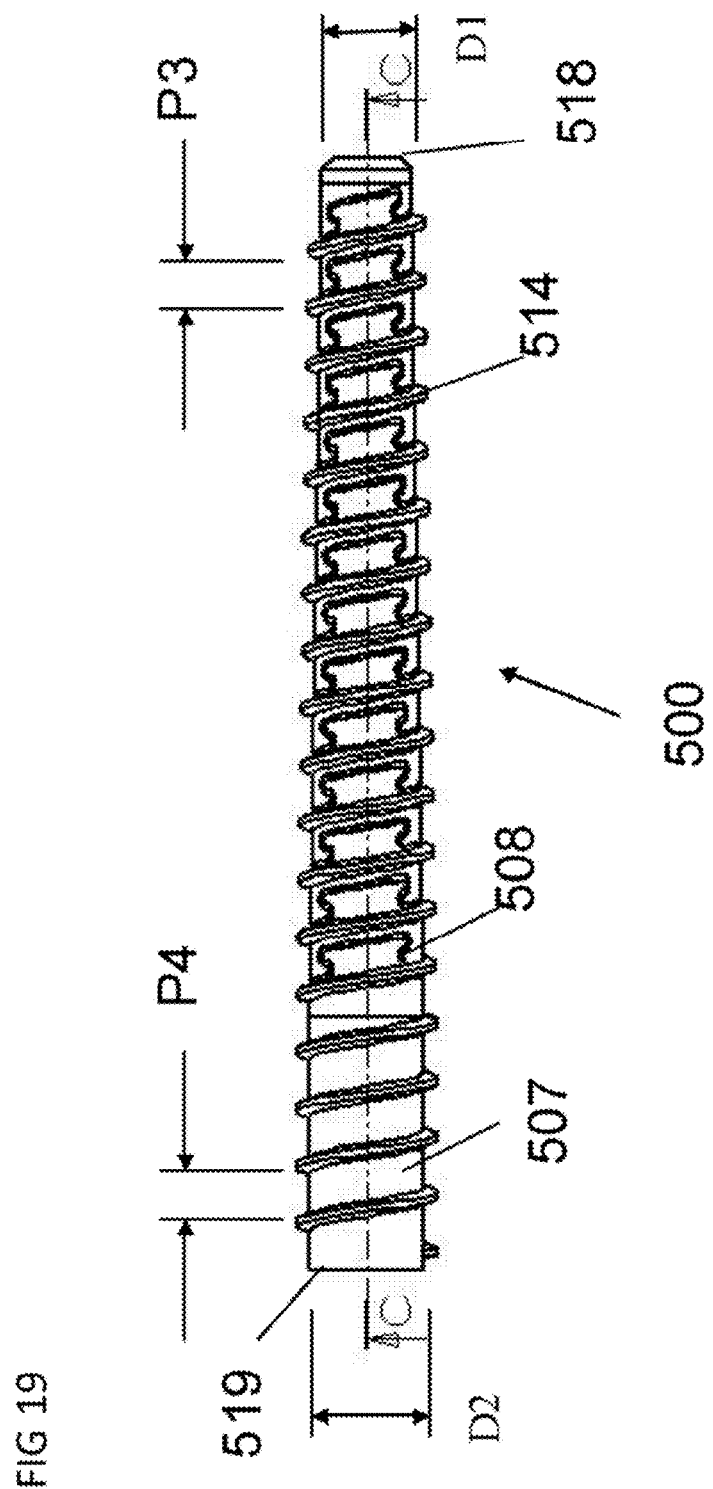
FIG. 19 is side elevation of the tapered compression device 100 in accordance with the invention.

FIG. 19 is the lateral elevation of the tapered flexible compression device 500 shown in FIG. 19. The thread 514 extends from the leading end 518 to the trailing end 519. In practice the pitch varies continuously over the length of the device 500 such that the leading pitch P3 is less than the trailing pitch P4 and intermediate pitches are less than proceeding thread pitch from the leading edge 518. Generally the pitch of the serpentine slot 508 will follow the pitch of the helical thread 514, but not necessarily. The serpentine slot 508 can have a pattern having about one to about 10 cycles per longitudinal revolution.

Figure 20:
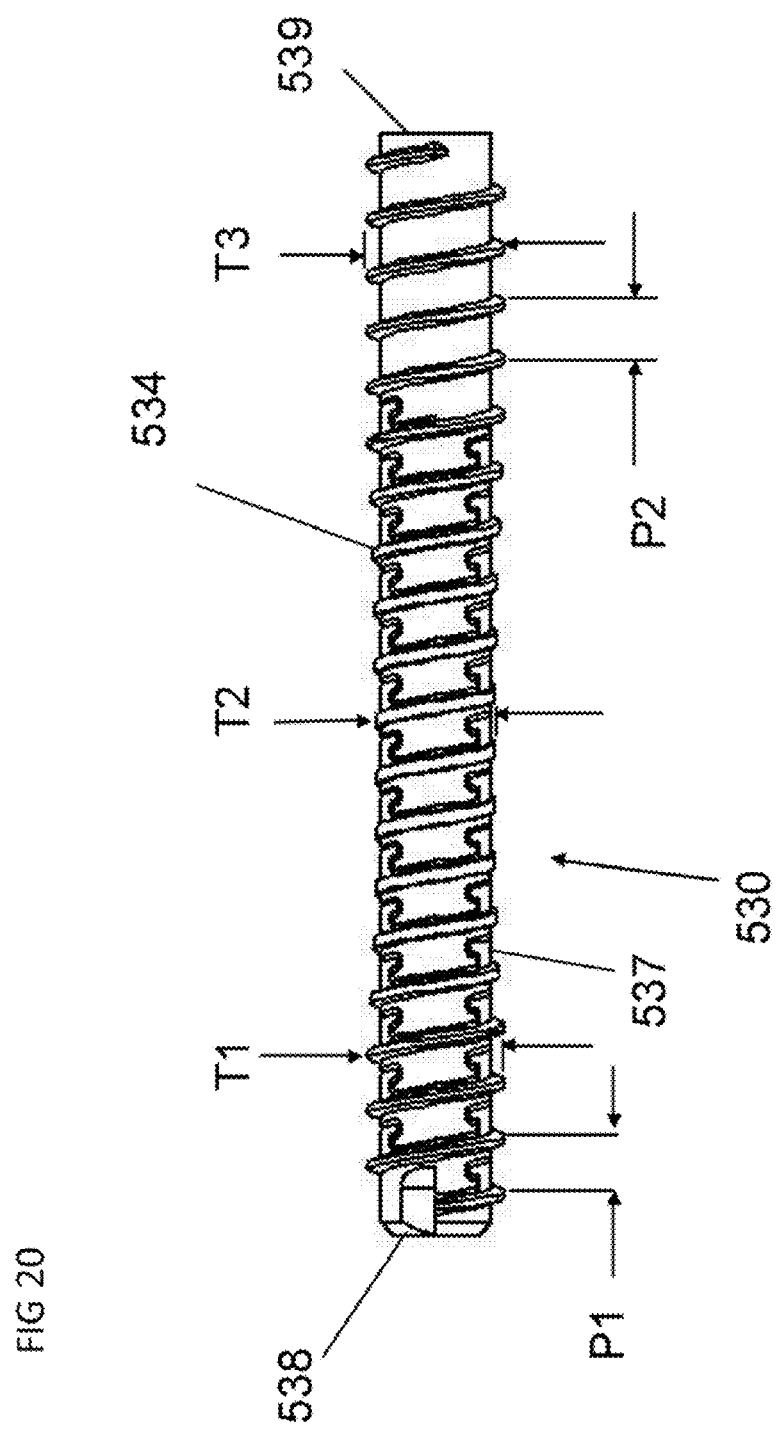
FIG. 20 is a side elevation of a variable radius thread compression device in accordance with the invention.
Figure 21G:
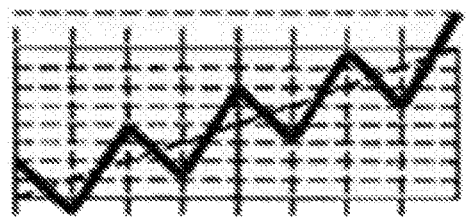
FIGS. 21A-21F show schematic representations of additional spiral slot patterns in accordance with the invention in accordance with the invention.
Figure 21H:
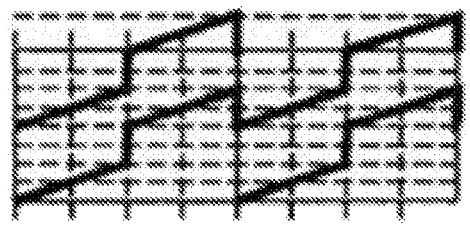
Figure 21I:
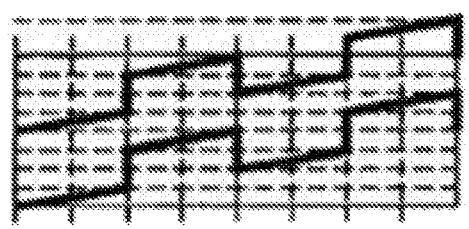
Figure 21J:
Figure 21K:
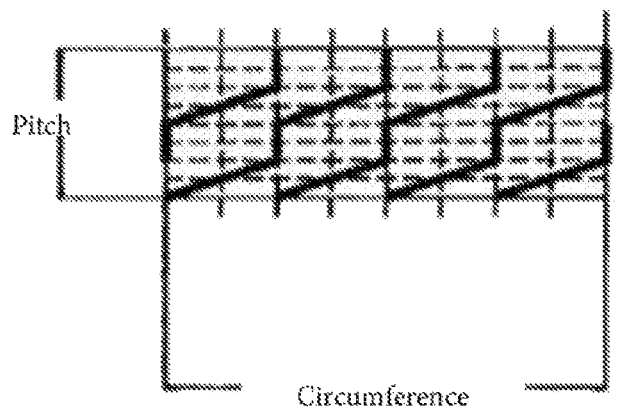

FIG. 20 illustrates another embodiment of a flexible compression device 530 having a variable thread height from the surface of the shaft 537 over the length of the device 530. The thread 534 which extends from the leading edge 538 has a major diameter T1 which decreases to T2 in the central segment and increases to T3 at a predetermined distance prior to the trailing edge 539. Typically the T3 is greater than T1 which is greater than T2. The reduced diameter T2 in the center of the device 530 helps to reduce the torque required to advance the device 530. In addition, the pitch may vary over the length of the device such that the pitch P1 of thread 534 is slightly greater than the pitch P2 of thread 534 at the trailing edge 539. As stated heretofore, the diameter of the device, and major D1 and minor D2 diameters of the thread are largely reliant on the end use.

A variety of slot patterns are illustrated in FIG. 21 A-K for use with any embodiment disclosed herein. The patterns are representative of patterns that can be used and are not intended to be all inclusive. As illustrated in FIG. 21A, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 21A and DTB for FIG. 21B. The pattern of 21C, does not provide dovetailing, and requires a helix angle that is relatively small. The pattern of FIG. 21G is an interrupted spiral in which the slot follows the helical path, deviates from the original angle for a given distance, and then resumes the original or another helix angle. Additional patterns, as shown in FIGS. 21D, 21E, 21F, 21H through 21K can have a configuration as illustrated in U.S. Pat. No. 6,447,518, the disclosure of which is incorporated herein by reference, as though recited in detail.

FIG. 22 illustrates another embodiment of a flexible compression device 550 in which the central segment 553 has two or more flexible segments 553A, 553B that can be at different helical angles 560', 560" as well as having different serpentine patterns of frequency and amplitude so as to have different flexibility. In addition, the general helical pattern can be in like rotational directions or may be in opposite rotational directions. As shown in this figure, the proximal segment 553A has a stiffer, less flexible segment than the distal segment 553B due to the reduction in frequency an amplitude. An additional feature in this embodiment is the addition of a hub 559 to the distal end of the leading segment 551 with a cutting notch 555' and having a diameter approximately equal to the major diameter D1 of thread 554 which has a minor diameter D2. In turn the central segment 553 has a diameter D3 approximately equal to the major diameter D1 of the leading segment thread 554 and hub 521. The threads 557 of the trailing segment 552 have a minor diameter D2' approximately equal to the diameter D3 of the central segment 553 and a major diameter D1'. A cutting notch 555" is located on the proximal end of the leading edge 551.

Figure 23:
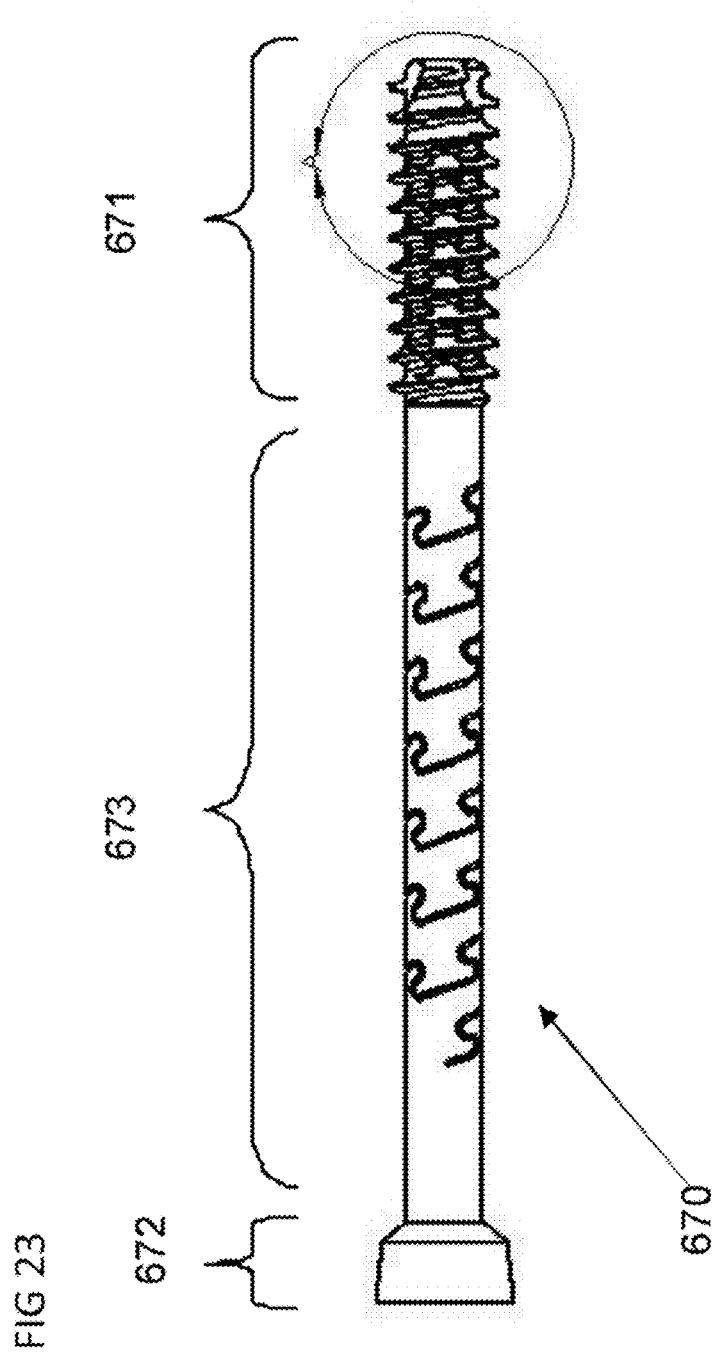
FIG. 23 is a side view off an alternate embodiment having a threaded leading edge having a slot that, in accordance with the invention in accordance with the invention.
Figure 24:
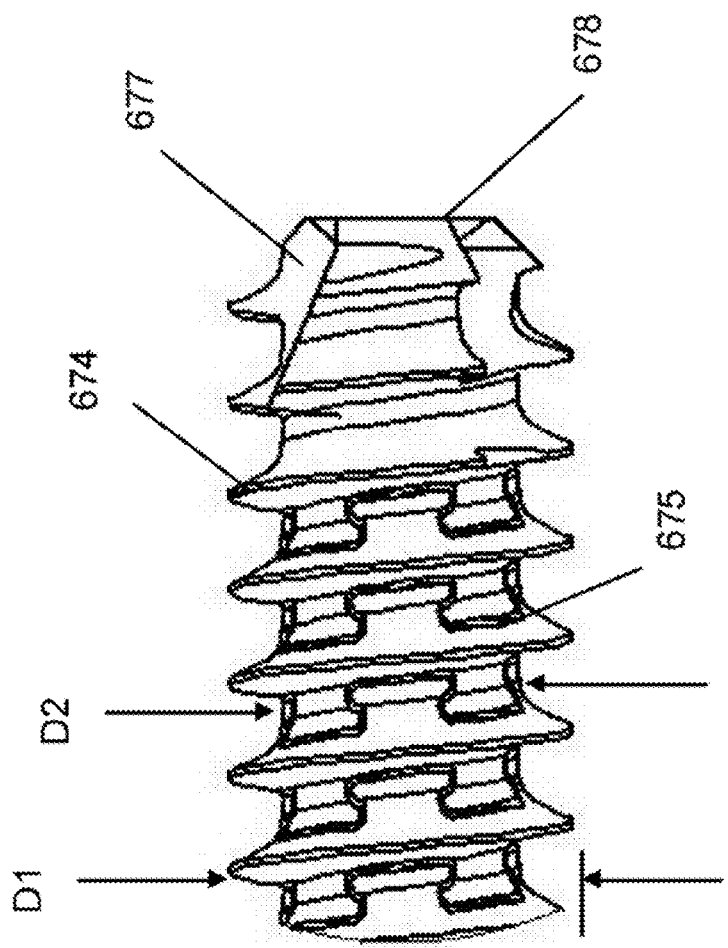
FIG. 24 is a view of the threaded portion of the threaded leading edge of FIG. 23 in accordance with the invention.

FIGS. 23 and 24 illustrate another embodiment of a flexible compression device 670 in which a flexible leading end segment 671 with helical serpentine slot 678 and a non threaded trailing end segment 672 axially spaced apart by a substantially cylindrical, flexible center segment 673 having a slot 678. The leading end segment 671 is furnished with a first screw thread 674 and a helical, serpentine slot 678. By mixing the type of slot and/or frequency, amplitude, etc., the flexibility of the device can be changed.

In the exploded view of section A in FIG. 23 shown in FIG. 24, the leading end segment 671 is furnished with a first screw thread 674 having a thread cutting recess 677 at the leading edge 678, and a helical, serpentine slot 675. In this instance, the helical serpentine slot 675 is formed on the minor diameter D2 of the threaded leading end segment 671 in FIG. 23. The slot can extend partially up the side of the thread 674 or up and over the thread 674.

Figure 25:
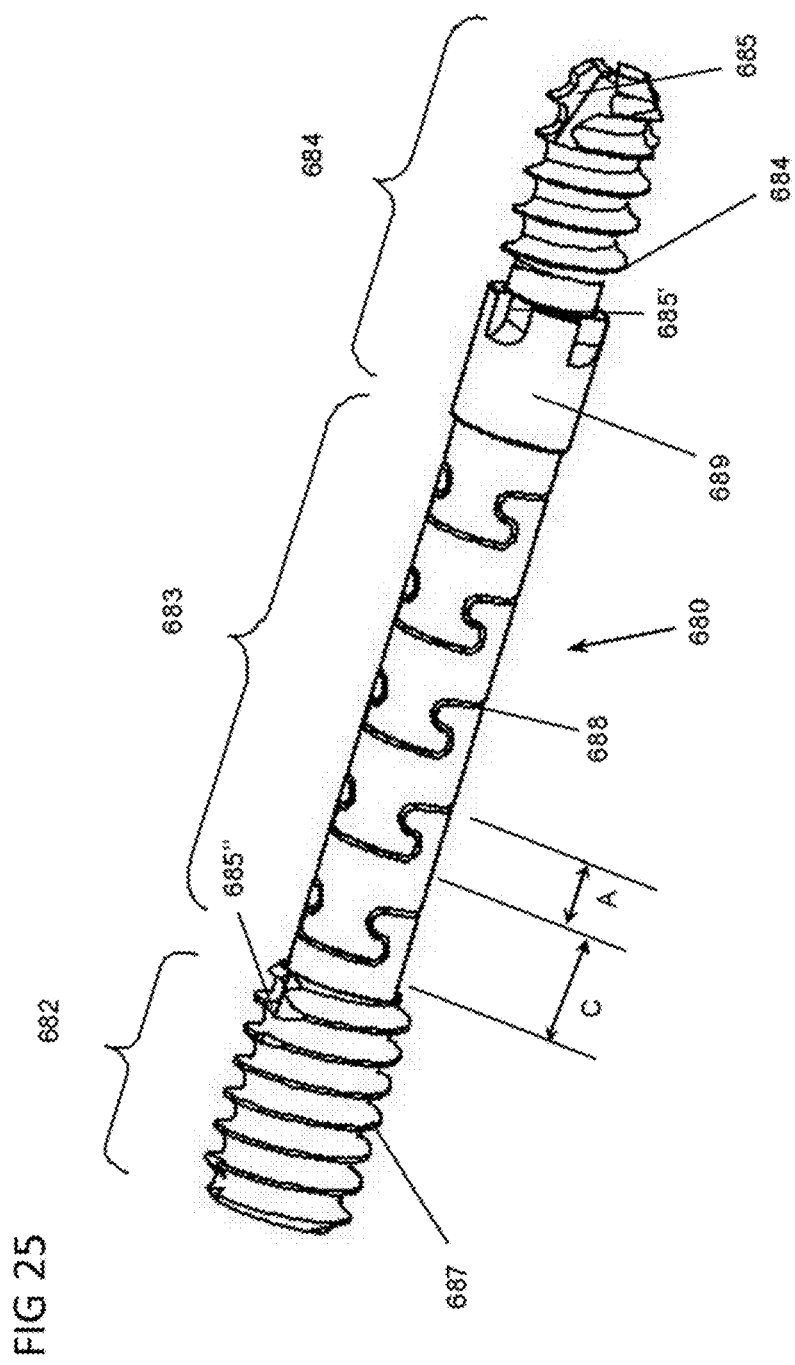
FIG. 25 is a side view of an additional embodiment of the flexible device in accordance with the invention in accordance with the invention.

FIG. 25 illustrates another embodiment of a flexible compression device 680 in which a leading threaded end segment 684, and a threaded trailing end segment 686 having threads 687, are axially spaced apart by a substantially cylindrical, flexible center segment 683 with one or more concentric slots 688. The concentric slot 688 has an amplitude A and spacing C from the previous slot. The leading end segment 684 is furnished with screw thread 691 and a thread cutting recess 685'. Between the leading end segment 684 and the center segment 683 is a collar 689 from which secondary cutting recess 685' is cut.

Figure 26:
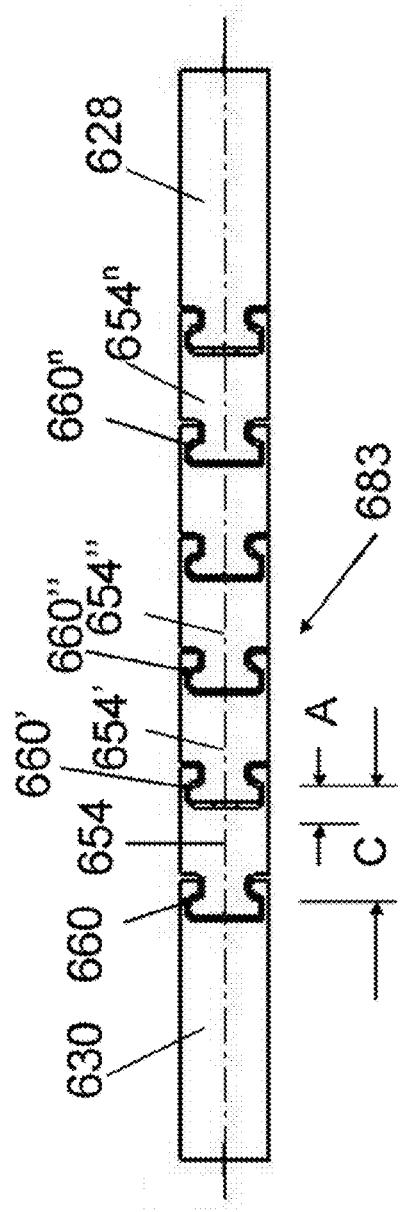
FIG. 26 is a schematic representation of the center segment 683 of FIG. 25, showing general pattern of the circumferential serpentine slots along the length of the rod in accordance with the invention in accordance with the invention.

In FIG. 26, the central segment 683 of FIG. 25 of the present invention generally consists of a hollow tube having a wall 652 with an outer surface 654 and a hollow central core 651 as illustrated in FIG. 28. A slots 660, 660', 660", . . . 660"' are cut through the wall 652, shown in FIG. 28, of segment of the central segment 683 to provide flexibility. Multiple circumferential slots 660', 660" . . . 660"' are situated continually at prescribed or varying intervals over all or most of the length of the segment 683 enabling the majority of the segment 683 to flex. The number of slots "n" can vary dependent upon the flexibility desired. The flexibility will be dependent upon the spacing "C" as well as the amplitude "A" of the serpentine slot 660 and the unslotted segment 654 between slots 660. In this embodiment the slots 660 . . . 660"' allow for flexibility only within the flexible segment. The segments 628 and 630 of the central segment 683 that are not slotted remain relatively rigid and are used for attachment with the leading and trailing segments In the embodiment illustrated in FIGS. 27, 28, and 29, the serpentine pattern of slot 660" is offset or staggered a rotational distance OFS from the adjacent slot 660"'. By staggering the serpentine pattern as illustrated, the bending characteristics, i.e. the bending strength and flexibility, can be changed to provide differences or uniformity with respect to the rotational axis.

The sectional view 27A-27A of central segment 683 of FIG. 25 is shown in FIG. 27. A magnified view 28B of the slot 660" is illustrated in FIG. 29. The slot 660" is representative of all the slots disclosed herein in that way that it is cut through the wall 652 into the core 651. Although the slots disclosed herein are of different patterns, this is purely a function of flexibility and all have the same basic construction. The criticality to the disclosed invention lies in the ratios and dimensions rather than the process of placing a rod or tube. In the following description of the criteria of the slots, no reference numbers specific to other figures are used, as the criteria are applicable to all slot configurations.

Figure 32:
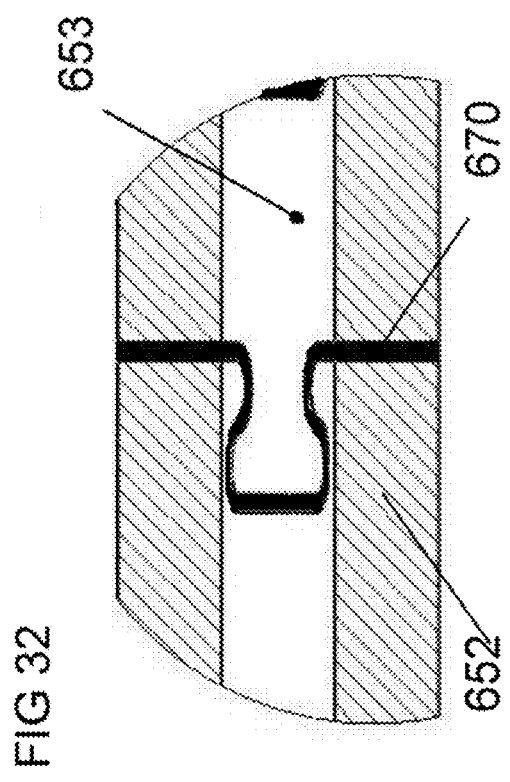
FIG. 32 is a magnified view of the area 31A in FIG. 31 in accordance with the invention in accordance with the invention.

In the embodiment illustrated in FIGS. 30, 31 and 32, a biocompatible resilient flexible or elastomeric material 670 has been added to the above device. The resilient material can be added to any of the embodiments disclosed herein in any of the configurations disclosed hereinafter. The elastomeric material 570 fills only the slot 660 of the central segment. The exterior surface 654 of the central segment remains uncovered by the material 670 as does the interior surface 653. The addition of the elastomeric material 670 to the slot 660 provides resistance to the flexibility of the segment 683 as well as preventing material from entering the slot or in the case of a medical device tissue and scar ingrowth into the slot. It should also be noted that the elastomeric material does not necessarily have to fill all slots in the rod, with the placement of filled and unfilled slots affecting the flexibility.

Figure 33:
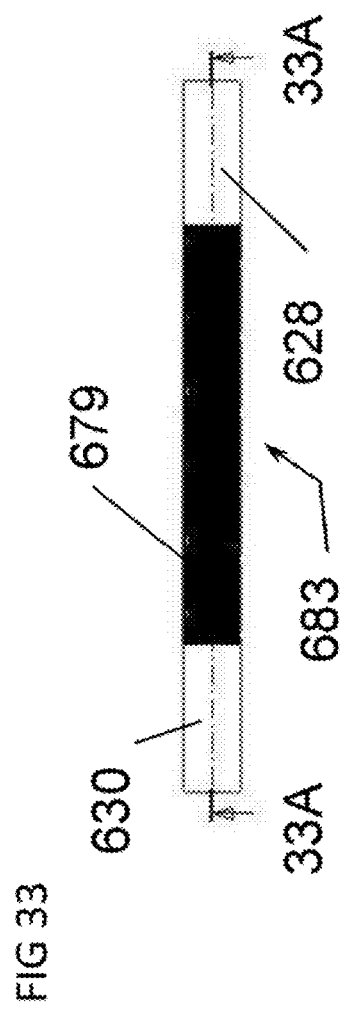
FIG. 33 is an exterior view of the central with the center portion encapsulated with a resilient filler in accordance with the invention.
Figure 34:
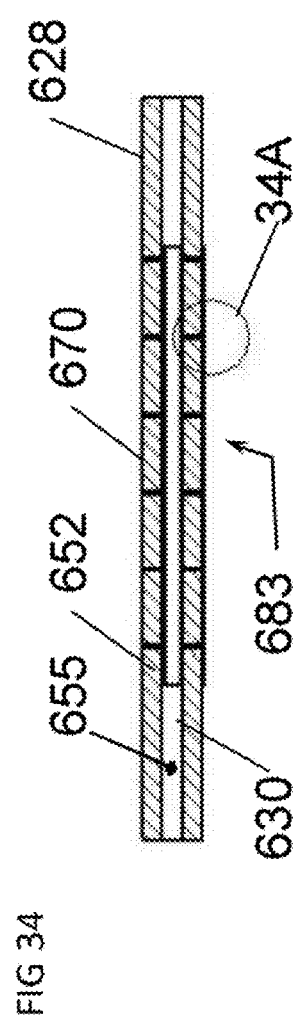
FIG. 34 is a sectional illustration though the longitudinal axis 33A-33A of the central segment in FIG. 33 showing the filled slot with a resilient filler encapsulating the entire segment but not filling the central core in accordance with the invention.
Figure 35:
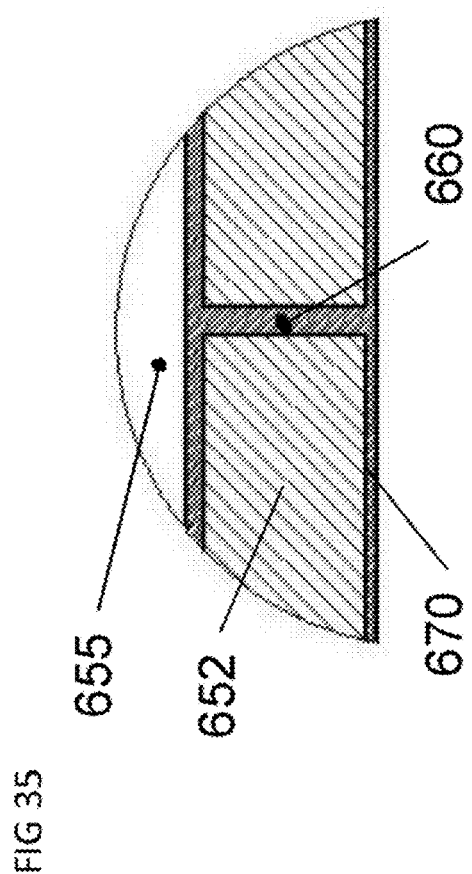
FIG. 35 is a magnified view of the area 34A in FIG. 34 in accordance with the invention.

In FIGS. 33, 34 and 35 the elastomeric material 670 encapsulates the central segment 683 as well as filling the slots 660. In this embodiment, the interior surface 653 and exterior surface 654 are covered with the elastomeric material 670 and the slots 660 are filled to prevent interposed material into the slots 660 and increase the stiffness of the device. The core 655, of the encapsulated segment 650, however, remains hollow as seen in section 33A-33A in FIG. 33. Although in these figures the elastomeric material 670 also fills the slots 660 passing through wall 652 as shown in FIG. 35 of the enlarged segment 34A, it should be noted that the elastomeric material 670 can alternatively only encapsulate the segment without filling the slots 660. Additionally, just the interior or exterior of the segment can be covered with the elastomeric material with the slots being either filled or unfilled. The encapsulation can be only at the portion of the device that is flexible or can extend the entire length of the rod. As noted above, the addition of the elastomeric material 670 increases the resistance to flexing and is not reflective of the advantages of encapsulating segment 650 with the elastomeric material 670.

Figure 36:
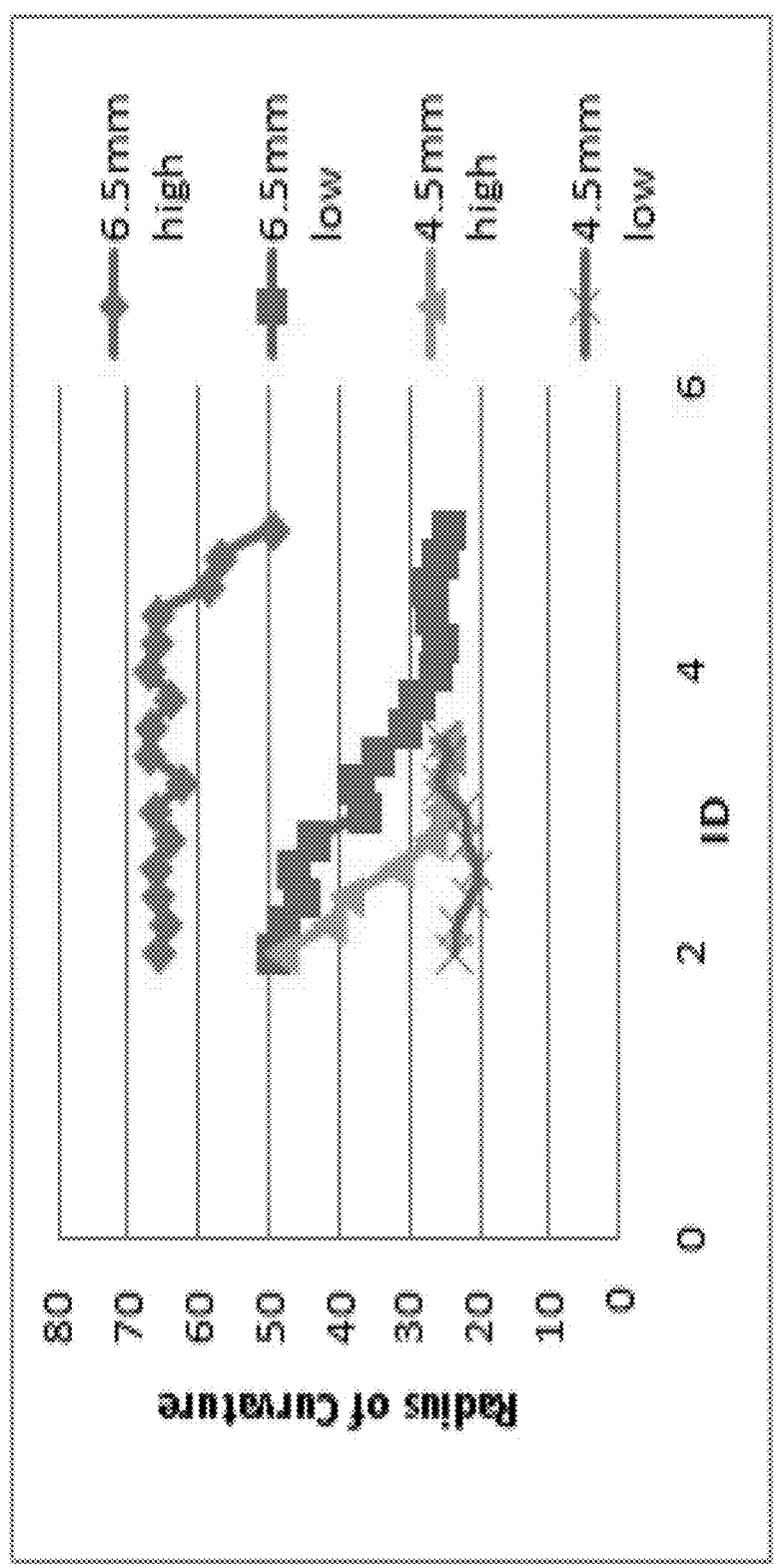
FIG. 36 is a graph illustrating the radius of curvature in accordance with the invention.

FIG. 36 Radius of Curvature (ROC) was determined from stress analysis performed on computer aided design flexible shafts of diameters 4.5 mm and 6.5 mm as a function the inner diameter of the shaft and the helix angle of the sinuous slot (low=9 deg, high=16 deg) which are typical of medical screw sizes. ROC and ID values are in millimeters As can be practiced, any of the segments of the flexible device can be either non-flexible or can be made flexible by the incorporation of a helical or concentric slot within the segment.

Computer aided design was used to model the flexible shaft of the devices and theoretical stress analysis (finite element analysis) and optimization techniques were used to determine the radius of curvature (ROC) of the flexible segment of the device as a function of the internal diameter of the shaft. A 4.5 and 6.5 mm outer diameter (OD) shaft was modeled with either a 9.0 (low) and 16 (high) degree helix pattern with an amplitude of 50% of the pitch with respect to increasing internal diameters (ID). The data generated is shown in FIG. 36 indicates the ROC decreased for the low helix angle screws with larger IDs. This means that the flexible segment could bend more with the lower helix angle slot than with a high angle slot. Also for a same outer diameter, the flexible segment with a larger inner diameter resulted in a more flexible segment. Thus for a given curved channel 330' as shown in FIGS. 11 and 12B, the flexible device 340 can be designed to conform to the curvature of the channel and pass through the channel easily. If the flexible segment had a ROC designed larger than the curvature of the channel, then the segment would be unable to pass through the channel 330', i.e. the segment would be too stiff and could not bend enough to pass through the channel. On the other hand, a segment 340 that is made with a lower ROC, i.e. more flexible, may be weaker than the optimum flexible segment as well as costing more to manufacture.

An application for the device shown in FIG. 1 may be one in which the device acts as a bolt connecting two components that will be subjected to vibration or impact loading. In this case the structure of the material between the helical, sinuous slot acts as a helical spring or shock absorbing device. The interdigitating path (interlocking, like the fingers of clasped hands) of the slot thus limits the longitudinal displacement between the two joined components. The flexible bolt thus allows minimum movement between the components and thus reduces the stresses and potential for failure.

An application of the compression device shown in FIG. 13 may be one in which the device acts as an intramedullary fixation screw for the reduction of bone fractures. In the case of a mid shaft fracture of the clavicle, a straight screw could not be placed in the intramedullary canal due to the double curvature of the bone. Thus a flexible screw 410 as shown in FIG. 13 could be introduced through a lateral entry point in the bone and passed through the intramedullary canal of the bone, pass the fracture and into the distal bone fragment. As the trailing end segment 412 enters the lateral bone fragment, the screw threads 416 engage the bone and, because of the different thread pitch compared to the leading threads 414, the lateral and distal bone fragments are drawn together thus stabilizing the fractured bone to promote healing. Compared to the traditional fixation of bone fractures with plates attached to the exterior surface with screws transverse to the bone's axis, this intramedullary fixation reduces operative complications inherent to plate and screw fixation.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

While in the foregoing embodiments of the invention have been disclosed in considerable detail, it will understood by those skilled in the art that many of these details may be varied without departing from the spirit and scope of the invention.

What is claimed is:

1. A flexible compression fastening device to secure two components adjacent one another, said flexible fastening device being a rigid material and having:
    a body, said body having a length and a diameter, said length to diameter aspect being at least 2 and multiple segments, at least one of said multiple segments being a hollow segment;
    at least one of multiple segments having exterior threads, and
    one of said multiple segments being a trailing segment having a receiving area to receive a rotational force device, and
    at least one of said at least one hollow segment having at least one helical, sinuous slot to form a flexible segment with sufficient flexibility to draw together and compress two components with curved or misaligned entry paths to be secured adjacent to one another.

2. The flexible device of claim 1 wherein said leading segment has at least one cutting recess.

3. The flexible device of claim 1 wherein said trailing segment has at least one cutting recess.

4. The flexible device of claim 1 said leading segment has threads.

5. The flexible device of claim 1 wherein said trailing segment has threads.

6. The flexible device of claim 1 wherein said leading segment and said trailing segment have threads, said threads of said leading segment having a different pitch and amplitude than said threads of said trailing portion.

7. The flexible device of claim 1 wherein said sinuous pattern is about 1 to about 10 cycles per longitudinal revolution.

8. The flexible device of claim 1 where wherein each of same multiple segments has a different diameter from adjoining segments.

9. The flexible device of claim 1 wherein said at least one helical, sinuous slot has a helical angle ranging from about 5 degrees to about 20 degrees.

10. The flexible device of claim 1 wherein: a. a first of said multiple segments is a leading segment, having said exterior threads, b. a second of said multiple segments is a center segment, having said helical, sinuous slot, c. a third of said multiple segments is said trailing threads.

11. A flexible compression fastening device to secure two components adjacent one another, said flexible fastening device being a rigid material and having
- a body, said body having a length and a diameter, said length to diameter aspect being at least 2, and multiple segments, at least one of said multiple segments being a hollow segment;
- at least one of said at least one hollow segment having at least one helical, sinuous slot along said hollow segment to form a flexible segment with sufficient flexibility to draw together and compress two components with curved or misaligned entry paths to be secured adjacent to one another, said sinuous pattern is about 1 to about 10 cycles per longitudinal revolution and said at least one helical sinuous slot has a helical angle ranging from about 5 degrees to about 20 degrees,
- one of said multiple segments being a leading segment, said leading segment having threads,
- at least one of multiple segments having exterior threads, and
- one of said multiple segments being a trailing segment having a receiving area to receive a rotational force device.

12. A method of securing two bodies requiring a curved entry path comprising the steps of:
- a. creating said entry path,
- b. selecting a flexible fastening device having a body, said body having a length to diameter aspect of at least 2, and multiple segments, at least one of said multiple segments being hollow and having at least one helical, sinuous slot; one of said segments have exterior threads and a trailing segment having a rotational force receiving area,
- c. inserting said flexible fastening device into said entry path
- d. rotating said flexible fastening device until said trailing edge is adjacent to a starting point of said entry path.

* * * * *